(12) United States Patent
Braido et al.

(10) Patent No.: US 9,566,146 B2
(45) Date of Patent: Feb. 14, 2017

(54) CARDIOVASCULAR VALVE AND VALVE HOUSING APPARATUSES AND SYSTEMS

(75) Inventors: Peter N. Braido, Maple Grove, MN (US); Yousef F. Alkhatib, Maple Grove, MN (US)

(73) Assignee: ST. JUDE MEDICAL, INC., St. Paul, MN (US)

( * ) Notice: Subject to any disclaimer, the term of this patent is extended or adjusted under 35 U.S.C. 154(b) by 105 days.

(21) Appl. No.: 12/340,189

(22) Filed: Dec. 19, 2008

(65) Prior Publication Data

US 2010/0161040 A1 Jun. 24, 2010

(51) Int. Cl.
| | |
|---|---|
| *A61F 2/24* | (2006.01) |
| *A61F 2/06* | (2013.01) |
| *A61B 17/11* | (2006.01) |
| *A61B 17/115* | (2006.01) |
| *A61B 17/3205* | (2006.01) |
| *A61M 1/10* | (2006.01) |

(Continued)

(52) U.S. Cl.
CPC ................ *A61F 2/06* (2013.01); *A61B 17/11* (2013.01); *A61B 17/1152* (2013.01); *A61B 17/32053* (2013.01); *A61F 2/064* (2013.01); *A61F 2/24* (2013.01); *A61M 1/10* (2013.01); *A61M 1/1008* (2014.02); *A61M 1/1096* (2014.02); *A61B 17/32002* (2013.01); *A61B 2017/00252* (2013.01); *A61B 2017/00349* (2013.01); *A61B 2017/00778* (2013.01); *A61B 2017/1107* (2013.01); *A61B 2017/1132* (2013.01); *A61B 2017/1135* (2013.01); *A61B 2090/061* (2016.02); *A61F 2/2403* (2013.01); *A61F 2/2409* (2013.01);

(Continued)

(58) Field of Classification Search
CPC ................ A61F 2/24; A61F 2250/0085; A61F 2250/0089
USPC ......................................................... 623/2.1
See application file for complete search history.

(56) References Cited

U.S. PATENT DOCUMENTS 3,232,577 A * 2/1966 Sargent ........................... 251/87
4,104,005 A * 8/1978 Poirier ........................... 417/394

(Continued)

FOREIGN PATENT DOCUMENTS

| WO | 9829146 | 7/1998 |
|---|---|---|
| WO | 2006019755 | 2/2006 |

OTHER PUBLICATIONS

Aeba, R., et al., "Apico-Pulmonary Artery Conduit Repair of Congenitally Corrected Transposition of the Great Arteries With Ventricular Septal Defect and Pulmonary Outflow Tract Obstruction: A 10-Year Follow-Up," Ann Thorac Surg, 2003, 76:1383-8 (Pages).

(Continued)

*Primary Examiner* — Jacqueline Woznicki
(74) *Attorney, Agent, or Firm* — Holland & Hart

(57) ABSTRACT

A cardiovascular valve assembly is disclosed including a housing assembly comprising a first portion and a second portion removably attached to the first portion. A valve may be positioned within the housing assembly. The valve, which may be a mechanical valve, a biological tissue valve, or a polymeric valve, may be structured to allow fluid to flow through the housing assembly in a single direction. In certain embodiments, the valve assembly may further include at least one coupling structure provided on the second portion and at least one aperture defined in the first portion, with the aperture structured to receive the coupling structure to couple the first portion to the second portion. Corresponding systems incorporating cardiovascular valve assemblies are also disclosed.

15 Claims, 17 Drawing Sheets

(51) Int. Cl.
  *A61B 17/32* (2006.01)
  *A61B 17/00* (2006.01)
  *A61F 2/30* (2006.01)
(52) U.S. Cl.
  CPC ............ *A61F 2/2412* (2013.01); *A61F 2/2475* (2013.01); *A61F 2002/30714* (2013.01); *A61F 2250/0089* (2013.01)

(56) References Cited

U.S. PATENT DOCUMENTS

| | | | |
|---|---|---|---|
| 4,397,617 A | 8/1983 | Sergio et al. | |
| 4,434,811 A * | 3/1984 | Murdoch | 137/515 |
| 4,769,031 A | 9/1988 | McGough et al. | |
| 4,790,844 A | 12/1988 | Ovil | |
| 4,816,029 A | 3/1989 | Penny, III et al. | |
| 4,872,874 A | 10/1989 | Taheri | |
| 5,269,764 A * | 12/1993 | Vetter et al. | 604/167.04 |
| 5,326,373 A * | 7/1994 | Nagase | 623/3.26 |
| 5,330,528 A | 7/1994 | Lazim | |
| 5,332,403 A | 7/1994 | Kolff | |
| 5,466,216 A | 11/1995 | Brown et al. | |
| 5,511,958 A | 4/1996 | Chen et al. | |
| 5,599,173 A | 2/1997 | Chen et al. | |
| 5,755,770 A | 5/1998 | Ravenscroft | |
| 5,776,185 A | 7/1998 | Verona et al. | |
| 5,810,708 A | 9/1998 | Woodard et al. | |
| 5,871,537 A | 2/1999 | Holman et al. | |
| 5,931,842 A | 8/1999 | Goldsteen et al. | |
| 5,941,908 A | 8/1999 | Goldsteen et al. | |
| 5,965,086 A | 10/1999 | Rose et al. | |
| 5,972,017 A | 10/1999 | Berg et al. | |
| 5,976,178 A | 11/1999 | Goldsteen et al. | |
| 6,001,056 A | 12/1999 | Jassawalla et al. | |
| 6,001,124 A | 12/1999 | Bachinski | |
| 6,013,190 A | 1/2000 | Berg et al. | |
| 6,016,810 A | 1/2000 | Ravenscroft | |
| 6,036,702 A | 3/2000 | Bachinski et al. | |
| 6,048,362 A | 4/2000 | Berg | |
| 6,059,823 A | 5/2000 | Holman et al. | |
| 6,059,827 A * | 5/2000 | Fenton, Jr. | 623/2.17 |
| 6,068,654 A | 5/2000 | Berg et al. | |
| 6,074,416 A | 6/2000 | Berg et al. | |
| 6,113,612 A | 9/2000 | Swanson et al. | |
| 6,120,432 A | 9/2000 | Sullivan et al. | |
| 6,136,007 A | 10/2000 | Goldsteen et al. | |
| 6,146,325 A | 11/2000 | Lewis et al. | |
| 6,152,937 A | 11/2000 | Peterson et al. | |
| 6,152,945 A | 11/2000 | Bachinski et al. | |
| 6,152,956 A | 11/2000 | Pierce | |
| 6,186,942 B1 | 2/2001 | Sullivan et al. | |
| 6,186,986 B1 | 2/2001 | Berg et al. | |
| 6,200,260 B1 | 3/2001 | Bolling | |
| 6,206,912 B1 | 3/2001 | Goldsteen et al. | |
| 6,235,054 B1 | 5/2001 | Berg et al. | |
| 6,261,315 B1 | 7/2001 | St. Germain et al. | |
| 6,273,880 B1 | 8/2001 | Berg et al. | |
| 6,293,965 B1 | 9/2001 | Berg et al. | |
| 6,299,575 B1 | 10/2001 | Bolling | |
| 6,302,905 B1 | 10/2001 | Goldsteen et al. | |
| 6,309,416 B1 | 10/2001 | Swanson et al. | |
| 6,319,276 B1 | 11/2001 | Holman et al. | |
| 6,346,071 B1 * | 2/2002 | Mussivand | 600/16 |
| 6,352,554 B2 | 3/2002 | De Paulis | |
| 6,371,982 B2 | 4/2002 | Berg et al. | |
| 6,387,037 B1 | 5/2002 | Bolling et al. | |
| 6,390,969 B1 | 5/2002 | Bolling et al. | |
| 6,416,527 B1 | 7/2002 | Berg et al. | |
| 6,428,464 B1 | 8/2002 | Bolling | |
| 6,432,131 B1 | 8/2002 | Ravenscroft | |
| 6,440,163 B1 | 8/2002 | Swanson et al. | |
| 6,443,884 B1 | 9/2002 | Miyawaki | |
| 6,450,171 B1 | 9/2002 | Buckberg et al. | |
| 6,451,033 B1 | 9/2002 | Berg et al. | |
| 6,451,048 B1 | 9/2002 | Berg et al. | |
| 6,475,222 B1 | 11/2002 | Berg et al. | |
| 6,508,252 B1 | 1/2003 | Berg et al. | |
| 6,508,822 B1 | 1/2003 | Peterson et al. | |
| 6,511,491 B2 | 1/2003 | Grudem et al. | |
| 6,514,196 B1 | 2/2003 | Sullivan et al. | |
| 6,533,812 B2 | 3/2003 | Swanson et al. | |
| 6,599,303 B1 | 7/2003 | Peterson et al. | |
| 6,610,004 B2 | 8/2003 | Viole et al. | |
| 6,613,087 B1 * | 9/2003 | Healy et al. | 623/2.14 |
| 6,620,176 B1 | 9/2003 | Peterson et al. | |
| 6,669,720 B1 | 12/2003 | Pierce | |
| 6,673,084 B1 | 1/2004 | Peterson et al. | |
| 6,692,523 B2 | 2/2004 | Holman et al. | |
| 6,702,829 B2 | 3/2004 | Bachinski et al. | |
| 6,726,648 B2 | 4/2004 | Kaplon et al. | |
| 6,746,463 B1 | 6/2004 | Schwartz | |
| 6,749,598 B1 | 6/2004 | Keren et al. | |
| 6,773,453 B2 | 8/2004 | Ravenscroft | |
| 6,802,806 B2 | 10/2004 | McCarthy et al. | |
| 6,805,692 B2 | 10/2004 | Muni et al. | |
| 6,863,677 B2 | 3/2005 | Breznock | |
| 6,889,082 B2 | 5/2005 | Bolling et al. | |
| 6,920,882 B2 | 7/2005 | Berg et al. | |
| 6,926,689 B2 | 8/2005 | Scheule | |
| 6,960,219 B2 | 11/2005 | Grudem et al. | |
| 6,994,666 B2 | 2/2006 | Shannon et al. | |
| 7,025,773 B2 | 4/2006 | Gittings et al. | |
| 7,029,483 B2 | 4/2006 | Schwartz | |
| 7,048,681 B2 | 5/2006 | Tsubouchi et al. | |
| 7,077,801 B2 | 7/2006 | Haverich | |
| 7,094,248 B2 | 8/2006 | Bachinski et al. | |
| 2001/0004675 A1 | 6/2001 | Woodard et al. | |
| 2001/0027287 A1 | 10/2001 | Scmulewitz et al. | |
| 2001/0049553 A1 | 12/2001 | De Paulis | |
| 2002/0040235 A1 | 4/2002 | Holman et al. | |
| 2002/0045846 A1 | 4/2002 | Kaplon et al. | |
| 2002/0128703 A1 | 9/2002 | Ravenscroft | |
| 2002/0198603 A1 | 12/2002 | Buckberg et al. | |
| 2003/0040765 A1 | 2/2003 | Breznock | |
| 2003/0083738 A1 | 5/2003 | Holman et al. | |
| 2003/0176830 A1 | 9/2003 | Scheule | |
| 2003/0208257 A1 | 11/2003 | Holman et al. | |
| 2003/0220684 A1 | 11/2003 | Holman et al. | |
| 2004/0059178 A1 | 3/2004 | McCarthy et al. | |
| 2004/0082910 A1 | 4/2004 | Constantz et al. | |
| 2004/0097900 A1 | 5/2004 | Keren et al. | |
| 2004/0162608 A1 | 8/2004 | Haverich | |
| 2004/0181126 A1 | 9/2004 | Buckberg et al. | |
| 2004/0193004 A1 | 9/2004 | Tsubouchi et al. | |
| 2004/0199191 A1 | 10/2004 | Schwartz | |
| 2004/0210202 A1 | 10/2004 | Weinstein | |
| 2004/0215321 A1 | 10/2004 | Holman et al. | |
| 2005/0119688 A1 | 6/2005 | Bergheim | |
| 2005/0149093 A1 | 7/2005 | Pokorney | |
| 2005/0154411 A1 | 7/2005 | Breznock et al. | |
| 2005/0209502 A1 | 9/2005 | Schmid et al. | |
| 2005/0251187 A1 | 11/2005 | Beane et al. | |
| 2005/0256363 A1 | 11/2005 | Bolling et al. | |
| 2005/0261759 A1 | 11/2005 | Lambrecht et al. | |
| 2006/0014999 A1 | 1/2006 | Heilman et al. | |
| 2006/0030747 A1 | 2/2006 | Kantrowitz et al. | |
| 2006/0036313 A1 | 2/2006 | Vassiliades | |
| 2006/0074271 A1 * | 4/2006 | Cotter | 600/16 |
| 2006/0079736 A1 | 4/2006 | Chin et al. | |
| 2006/0089707 A1 | 4/2006 | Vassiliades et al. | |
| 2006/0161133 A1 | 7/2006 | Laird et al. | |
| 2006/0161193 A1 | 7/2006 | Beane et al. | |
| 2007/0010834 A1 * | 1/2007 | Sharkawy et al. | 606/153 |
| 2007/0055357 A1 * | 3/2007 | Pokorney et al. | 623/1.26 |
| 2010/0160832 A1 | 6/2010 | Braido | |
| 2010/0160847 A1 | 6/2010 | Braido et al. | |

OTHER PUBLICATIONS

Behrendt, D., et al., "Relief of left ventricular outflow tract obstruction in infants and small children with valved extra cardiac conduits," Ann Thorac Surg., 1987; 43(1):82-6 (Pages).

(56) References Cited

OTHER PUBLICATIONS

Bickers, G., et al., "Gastroesophageal deformities of left ventricular-abdominal aortic conduit," AJR Am J Roentgenol, May 1982; 138(5):867-9 (Pages).

Marino, S. Bradley, et al., "Early Results of the Ross Procedure in Simple and Complex Left Heart Disease," Circulation, 1999; 10:II-162-6 (Pages).

Brown, J., et al., "Long-Term Results of Apical Aortic Conduits in Children With Complex Left Ventricular Outflow Tract Obstruction," Ann Thorac Surg., 2005; 80:2301-8 (Pages).

Ugorji, C., et al., "Post-Traumatic Apical Left Ventricular Aneurysm in a Patient with Left Ventricular Apical-Abdominal Aortic Conduit: Case Presentation," Cardiovascular Diseases, Bulletin of the Texas Heart Institute, 1979; 6:4 (Pages).

Crestanello, J., et al., "Is there a role for the left ventricle apical-aortic conduit for acquired aortic stenosis?", J Heart Valve Dis. Jan. 2004; 13(1):57-62; discussion 62-3 (Pages).

Cooley, Denton, A., et al., "Left Ventricle to Abdominal Aorta Conduit for Relief of Aortic Stenosis," Cardiovascular Diseases, Bulleting of the Texas Heart Institute, 1975, 2; 3 (Pages).

Fogel, M., et al, "Evaluation and follow-up of patients with left ventricular apical to aortic conduits with 2D and 3D magnetic resonance imaging and Doppler echocardiography: A new look at an old operation," American Heart Journal, 2001; 141:630-6 (Pages).

Frommelt, P., et al., "Natural history of apical left ventricular to aortic conduits in pediatric patients," Circulation, Nov. 1991; 84(5Suppl):III213-8 (Pages).

Gammie, J., et al., "Aortic valve bypass for the high-risk patient with aortic stenosis," Annals of Thoracic Surgery, 2006; 81:1605-1611 (Pages).

Koul, B., et al., "Aortoventriculoplasty ad modem Konno. Experience with five cases," Scand J. Thorac Cardiovasc Surg., 1984; 18(3):239-42 (Pages).

Misbach, G., et al., "Left ventricular outflow enlargement by the Konno procedure," Journal of Thoracic Cardiovascular Surgery, Nov. 1982; 84(5):696-703 (Pages).

Miyawaki, F., et al., "Recovery directed left ventricular assist device; a new concept," ASAIO J, May-Jun. 2000; 46(3):361-6 (Pages).

Norwood WI, et al., "Management of infants with left ventricular outflow obstruction by conduit interposition between the ventricular apex and thoracic aorta," J Thorac Cardiovasc Surg., Nov. 1983; 86(5):771-6 (Pages).

Rocchini, A., at al., "Clinical and hemodynamic follow-up of left ventricular to aortic conduits in patients with aortic stenosis," J Am Coll Cardiol., Apr. 1983; 1(4):1135-43 (Pages).

Serraf, A., et al., "Surgical Treatment of Subaortic Stenosis: A Seventeen-Year Experience," J Thorac Cardiovasc Surg., 1999; 117:669-78 (Pages).

Vassiliades, T., "Off-pump apicoaortic conduit insertion for high-risk patients with aortic stenosis," European Journal of Cardio-thoracic Surgery, 2003; 23:156-8 (Pages).

Vigano, M., et al., "Modified method for Novacor left ventricular assist device implantation," Ann Thorac Surg., Jan. 1996; 61(1):247-9 (Pages).

PCT International Search Report for International Application No. PCT/US2009/006581, mailed Mar. 17, 2010 (3 pp.).

* cited by examiner

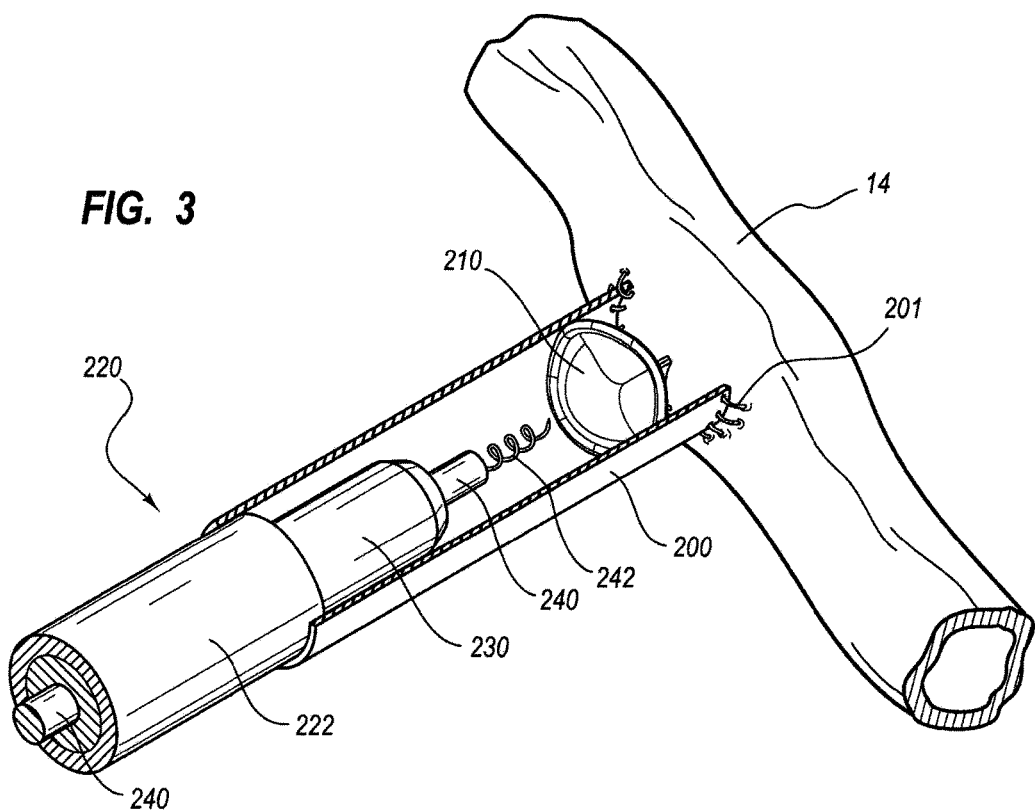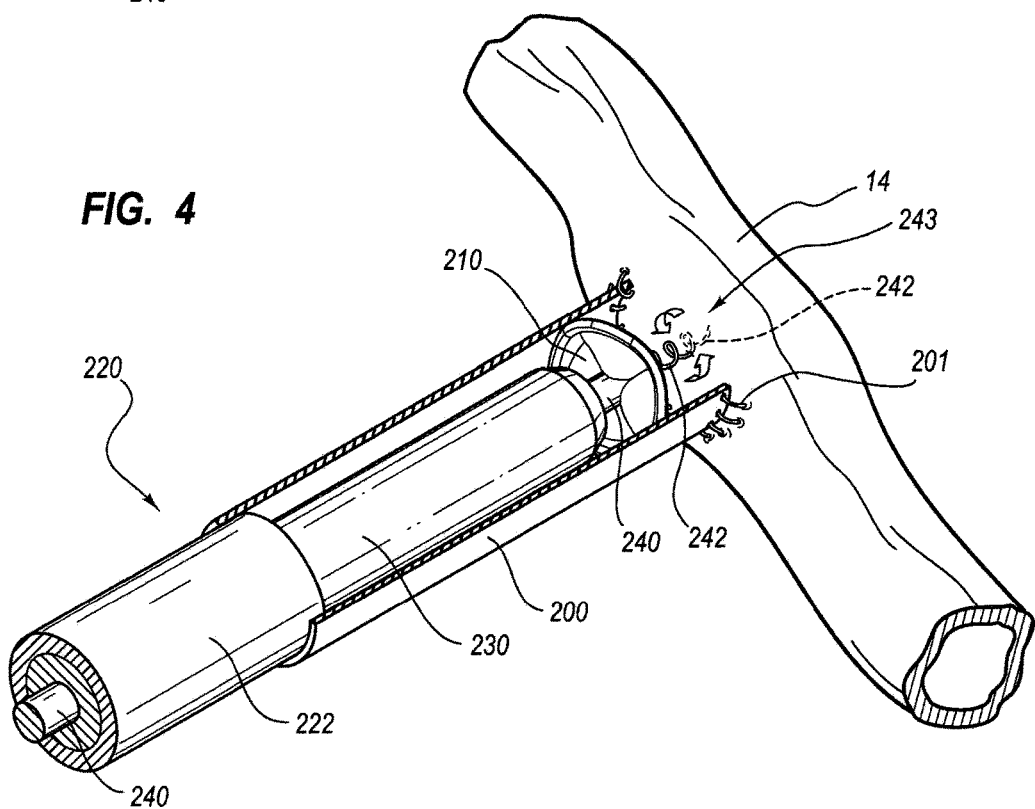

CARDIOVASCULAR VALVE AND VALVE HOUSING APPARATUSES AND SYSTEMS

BACKGROUND

Aortic valve replacement is a cardiac surgery procedure that replaces a patient's aortic valve with a prosthetic valve. Aortic valve replacement typically requires open heart surgery, which may be risky and/or impractical for many patients. Aortic valve replacement may not be an option for patients with aortic stenosis, left ventricular outflow obstruction, a heavily calcified ascending aorta, a heavily calcified aortic root, and/or other high risk medical conditions. For example, patients with conditions that preclude a median sternotomy may not be candidates for an aortic valve replacement operation.

Apical aortic conduits may provide a less invasive alternative to aortic valve replacement. An apical aortic conduit may be connected between the apex of the heart and the aorta in a procedure similar to a coronary artery bypass graft. Apical aortic conduits may improve blood flow between the heart and the aorta by bypassing a diseased or malfunctioning aortic valve. Patients who are not eligible for aortic valve replacement may be treated by using an apical aortic conduit to bypass the valve. For example, apical aortic conduits may be used in pediatric patients. The native valve may be left in place in pediatric patients to eliminate the need for periodic valve replacements as the patient grows. Thus, the apical aortic conduit may maintain the maximum possible function of the native valve while bypassing the restricted flow to lessen stress on the heart and allow more blood flow to the body. In other words, the apical aortic conduit may bypass the native valve to allow for extra flow to the aorta while still allowing the maximum flow that the native valve can physiologically handle.

Traditional apical aortic conduits may fail or malfunction for various reasons. For example, the conduit material used in an apical aortic conduit may become blocked as a result of kinking. Traditional conduits may also become occluded and obstruct apical flow. Also, apical aortic conduits are typically sutured to the heart and the aorta, and the suturing may cause aneurisms at or near the attachment site. Apical aortic conduits may also cause gastrointestinal complications such as dysphagia and gastric erosion. Furthermore, implanting an apical aortic conduit on a beating heart may result in significant blood loss from the patient.

SUMMARY

In at least one embodiment, a cardiovascular valve assembly may comprise a housing assembly comprising a first portion and a second portion removably attached to the first portion. The cardiovascular valve assembly also may comprise a valve positioned within the housing assembly. In certain embodiments, the valve may be structured to allow fluid to flow through the housing assembly in a single direction. The valve may comprise at least one of a mechanical valve, a biological tissue valve, and a polymeric valve.

In certain embodiments, the first portion may comprise a first connector structured to removably attach the first portion to a first conduit. Similarly, the second portion may comprise a second connector structured to removably attach the second portion to a second conduit. In at least one embodiment, the valve may be a biological tissue valve comprising a cuff member positioned between the first portion and the second portion.

In certain embodiments, the cardiovascular valve assembly may further comprise at least one coupling structure provided on the second portion and at least one aperture defined in the first portion, the aperture being structured to receive the coupling structure to couple the first portion to the second portion. In addition, the coupling structure provided on the second portion may be configured to snap-fit into the aperture defined in the first portion. At least one aperture also may be defined in the valve. In this embodiment, the apertures defined in the first portion in the valve may be structured to receive the coupling structure provided on the second portion to couple the first portion and the valve to the second portion.

In an additional embodiment, the cardiovascular valve assembly may further comprise a hinged structure constructed to hingedly attach the first portion to the second portion. The valve assembly also may further comprise at least one seal member positioned between the first portion and the second portion, the seal member being configured to prevent fluid from escaping the housing assembly. In addition, when the first portion is removably attached to the second portion, the first and second portions may form a seal to prevent fluid from escaping the housing assembly.

In at least one embodiment, the cardiovascular valve assembly also may comprise at least one identifying indicia to identify a direction for fluid flow. In addition, the valve may be structured to prevent the valve from being positioned within the housing assembly in a manner that restricts fluid flow in a desired direction.

In an additional embodiment, the first portion may comprise a contoured contact surface structured to contact a contoured contact surface formed on the second portion. The cardiovascular valve assembly also may comprise a threaded end provided on the first portion and a threaded recess defined in the second portion, the threaded recess being structured to receive the threaded end to removably attach the first portion to the second portion. The cardiovascular valve assembly also may comprise a retention assembly configured to removably secure the first portion to the second portion. In addition, the valve may be sutured to at least one of the first portion and the second portion. The first portion also may be stapled to the second portion. In addition, the first portion and the second portion may comprise conical-shaped ends configured to contact at least a portion of the valve.

In an additional embodiment, a pre-assembled cardiovascular valve assembly may comprise a conduit, a housing assembly positioned within the conduit, and a valve positioned within the housing assembly. In certain embodiments, the housing assembly may be sutured to the conduit. In addition, the valve may be structured to allow fluid to flow through the housing assembly in a single direction. The valve may comprise at least one of a mechanical valve, a biological tissue valve, and a polymeric valve.

In certain embodiments, a system may comprise a first conduit dimensioned to be positioned against a first coring site of a cardiovascular organ and a valve assembly removably attached to the first conduit. The valve assembly may comprise a housing assembly comprising a first portion and a second portion removably attached to the first portion and a valve positioned within the housing assembly. The valve may be structured to allow fluid to flow through the housing assembly in a single direction. In addition, the system may comprise a second conduit removably attached to the valve assembly. The second conduit may be dimensioned to be positioned against a second coring site of a cardiovascular organ.

In at least one embodiment, a cardiovascular valve assembly may comprise a housing assembly, the housing assembly comprising a first portion comprising at least one coupling structure and a second portion comprising at least one aperture. In certain embodiments, this aperture may be structured to receive the coupling structure to removably attach the first portion to the second portion. In addition, the cardiovascular valve assembly may comprise a valve positioned within the housing assembly, at least one seal member positioned between the first portion and the second portion, and at least one identifying indicia configured to indicate a desired direction for fluid flow. In certain embodiments, the seal member may be configured to prevent fluid from escaping the housing assembly. In addition, the valve may be structured to allow fluid to flow through the housing assembly in a single direction. The valve also may be structured to prevent the valve from being positioned within the housing assembly in a manner that restricts fluid flow in a desired direction.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 3 is a perspective view of an exemplary cardiovascular coring device being inserted into the tube illustrated in FIG. 2.

FIG. 4 is a perspective view of the cardiovascular coring device illustrated in FIG. 3

Figure 1:
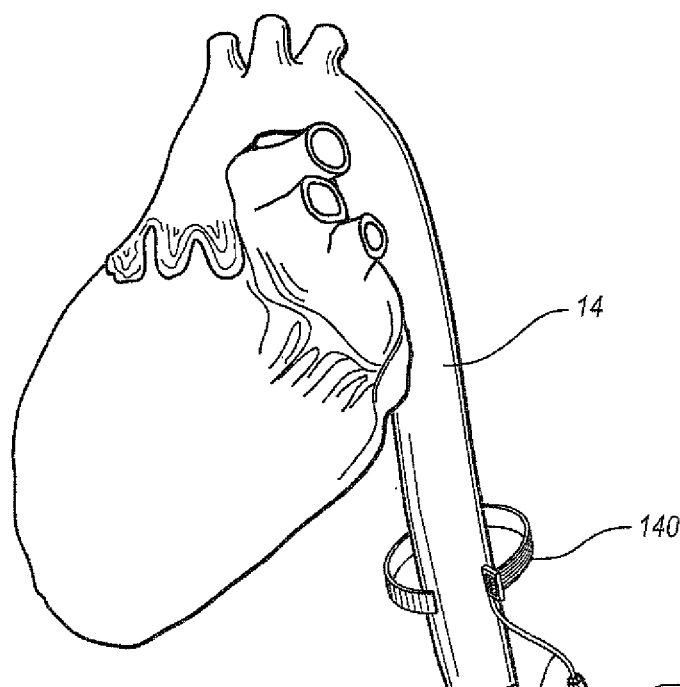
FIG. 1 is a perspective view of a heart, an aorta, and an aorta measuring device according to certain embodiments.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

A physician may implant a cardiovascular conduit system to circumvent a restriction in blood flow. For example, a physician may use a cardiovascular conduit system to bypass an aortic valve in a patient with aortic valve stenosis. Similarly, a cardiovascular conduit system may be used to bypass a pulmonary valve in a patient with pulmonary valve stenosis. Physicians may also use cardiovascular conduit systems to address various other problems and diseases in a patient's cardiovascular system.

Cardiovascular conduit systems may provide various advantages over prior systems. Physicians may implant a cardiovascular conduit system on a beating heart. Procedures performed on a beating heart may be referred to as off-pump procedures, and off-pump procedures may be less invasive than on-pump procedures (i.e., procedures that require cardiopulmonary bypass). In some embodiments, cardiovascular conduit systems may be used with traditional surgical techniques (e.g., on-pump procedures). In traditional surgical techniques, cardiovascular conduit systems may provide various advantages, such as reduced pump time and smaller incisions. Connectors in a cardiovascular conduit system may be designed to reduce the risk of aneurisms at the attachment site. The conduit in a cardiovascular conduit system may be kink and occlusion resistant. Cardiovascular conduit systems may also reduce the risk of gastrointestinal complications. Cardiovascular conduit systems may be implanted quickly and minimize patient blood loss. The following disclosure presents numerous other features and advantages of cardiovascular conduit systems.

The process of implanting a cardiovascular conduit system in a patient may involve a variety of steps. FIGS. 1-11 illustrate an exemplary process for implanting a cardiovascular conduit system between an apex of a heart and an aorta. The first step in implanting a cardiovascular conduit system may be measuring the size of a patient's aorta. A physician may determine the size of the patient's aorta to determine the appropriate sizes for the coring device and aortic connector that will be used in the procedure.

FIG. 1 illustrates an aorta measuring device 100 for measuring a circumference of an aorta 14. Aorta measuring device 100 may include a handle 110, an extension 120, and a circular measuring member 140. A physician may position measuring member 140 around aorta 14. The physician may then tighten measuring member 140 until it is snug around aorta 14 and capable of measuring the circumference of aorta 14. The physician may then take a measurement from measuring member 140. Various examples of aorta measuring devices are illustrated and described in U.S. patent application Ser. No. 12/340,382, filed on 19 Dec. 2008, and entitled "Apparatus and Method for Measuring Blood Vessels," the disclosure of which is incorporated in its entirety by this reference.

Figure 2:
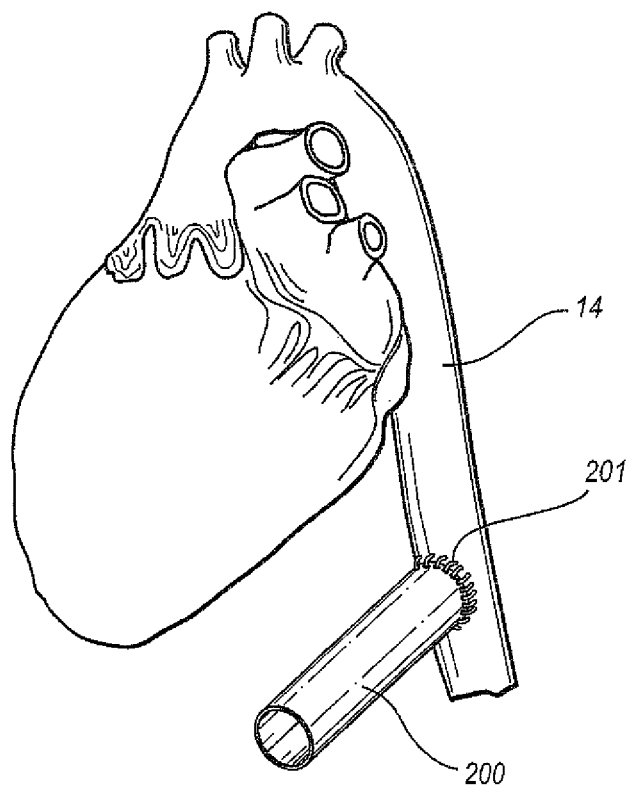
FIG. 2 is a perspective view of an exemplary tube attached to an aorta according to certain embodiments.

After determining the size of a patient's aorta, the physician may select the appropriately sized connector, conduit, valve, coring device, tube, and/or other tools for implanting the cardiovascular conduit system. FIG. 2 shows an end of a tube 200 attached to aorta 14. As shown in FIGS. 3-8, tube 200 may provide a sealed interface with aorta 14 during various steps in the process of implanting a cardiovascular conduit system. Tube 200 may be any suitable size and/or shape. As shown in FIG. 2, tube 200 may be cylindrical. In other embodiments, tube 200 may have a rectangular shape, square shape, triangular shape, or any other suitable shape. Tube 200 may be any suitable length and may be made of any suitable material (e.g., metal, plastic, etc.). Tube 200 may be any suitable type of duct, conduit, pipe, channel, or other enclosure designed to provide a sealed interface between an aorta and various cardiovascular conduit system parts and tools.

As shown in FIG. 2, tube 200 may be sutured to aorta 14 by sutures 201. Sutures 201 may hold tube 200 in place and may help prevent blood leakage at the interface between aorta 14 and tube 200. Tube 200 may be secured to aorta 14 using any suitable attachment mechanism in addition to or instead of sutures. For example, tube 200 may be secured to aorta 14 using a clamp that wraps around aorta 14. In other embodiments, a physician may press tube 200 against aorta 14 without using any additional attachment mechanism.

A physician may insert a coring device into tube 200 after attaching tube 200 to aorta 14. FIG. 3 shows a cross-sectional view of tube 200. FIG. 3 also illustrates a cardiovascular coring device 220 being inserted into tube 200. Cardiovascular coring device 220 may include a handle 222, a cutting member 230, a tissue retraction member 240, and a corkscrew anchor 242. Corkscrew anchor 242 may extend from tissue retraction member 240. Tissue retraction member 240 may extend through cutting member 230 and handle 222.

Figure 5:
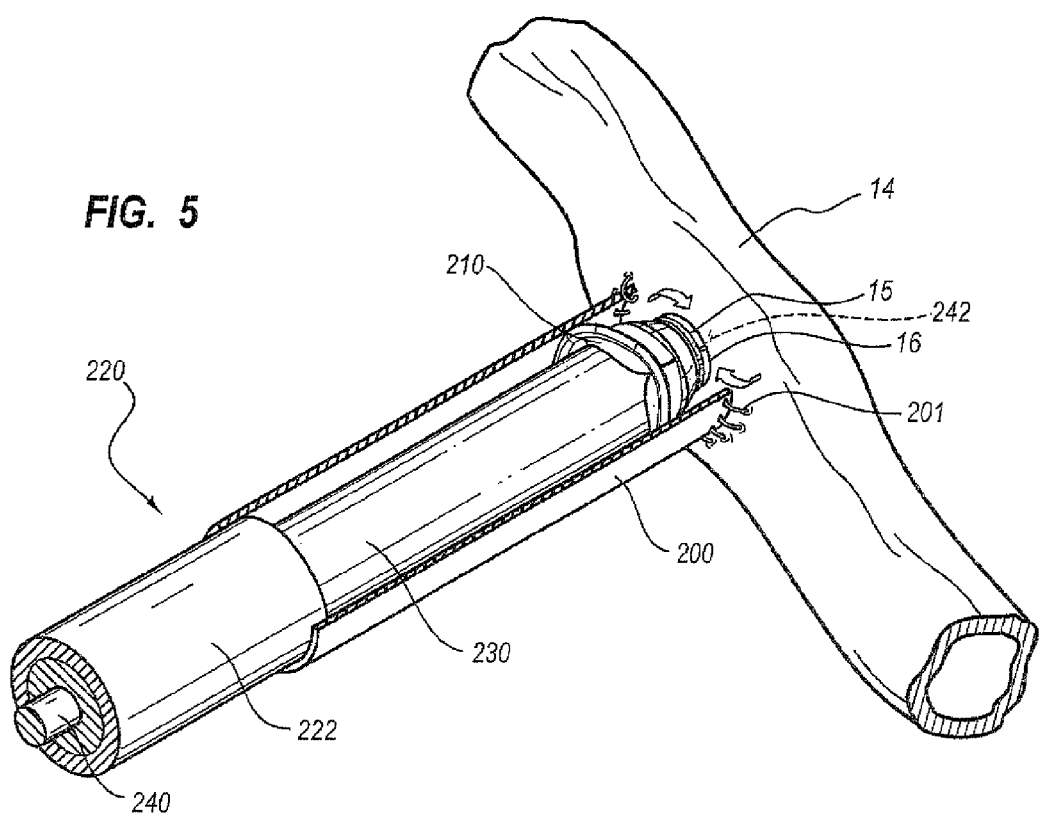
FIG. 5 is another perspective view of the cardiovascular coring device illustrated in FIG. 3.

A valve 210 may be positioned within tube 200. Valve 210 may be attached to tube 200. In other embodiments, valve 210 may be formed as part of tube 200. Valve 210 may be a one-way valve that allows cardiovascular coring device 220 to pass through but blocks the flow of blood out of the opening cut in aorta 14. Valve 210 may also seal cutting member 230 to tube 200 (as shown in FIG. 5) to prevent blood from leaking between tube 200 and cutting member 230. FIGS. 14-25 illustrate various examples of valves that may be used in a delivery tube.

FIG. 4 illustrates corkscrew anchor 242 being rotated into aorta 14 at a coring site 243. Corkscrew anchor 242 may be secured to the section of tissue that will be removed from aorta 14. Corkscrew anchor 242 may prevent the section of tissue from entering the blood stream in aorta 14. Various other types of anchors may be secured to cardiovascular organ tissue, as will be discussed in the disclosure corresponding to FIGS. 12-24.

FIG. 5 shows cardiovascular coring device 220 cutting an opening in aorta 14. Valve 210 may seal cutting member 230 to tube 200 while cutting member 230 cuts the opening in aorta 14. Cutting member 230 may rotate to cut the opening in aorta 14. In some embodiments, cutting member 230 may be directly connected to handle 222, and a physician may rotate cutting member 230 by rotating handle 222. In other embodiments, cutting member 230 may be rotated by an electric motor or any other suitable rotating mechanism.

According to various embodiments, cutting members may be any cutting devices suitable for cutting a cardiovascular organ. A cutting member may be a mechanical coring device, as illustrated in FIG. 5. A cutting member may also be a laser scalpel, a high-frequency ultra-sound device, or any other suitable type of cutting device. Cutting members may be standalone devices. In other embodiments, a cutting member may be incorporated into a cardiovascular coring device or any other suitable device.

Figure 6:
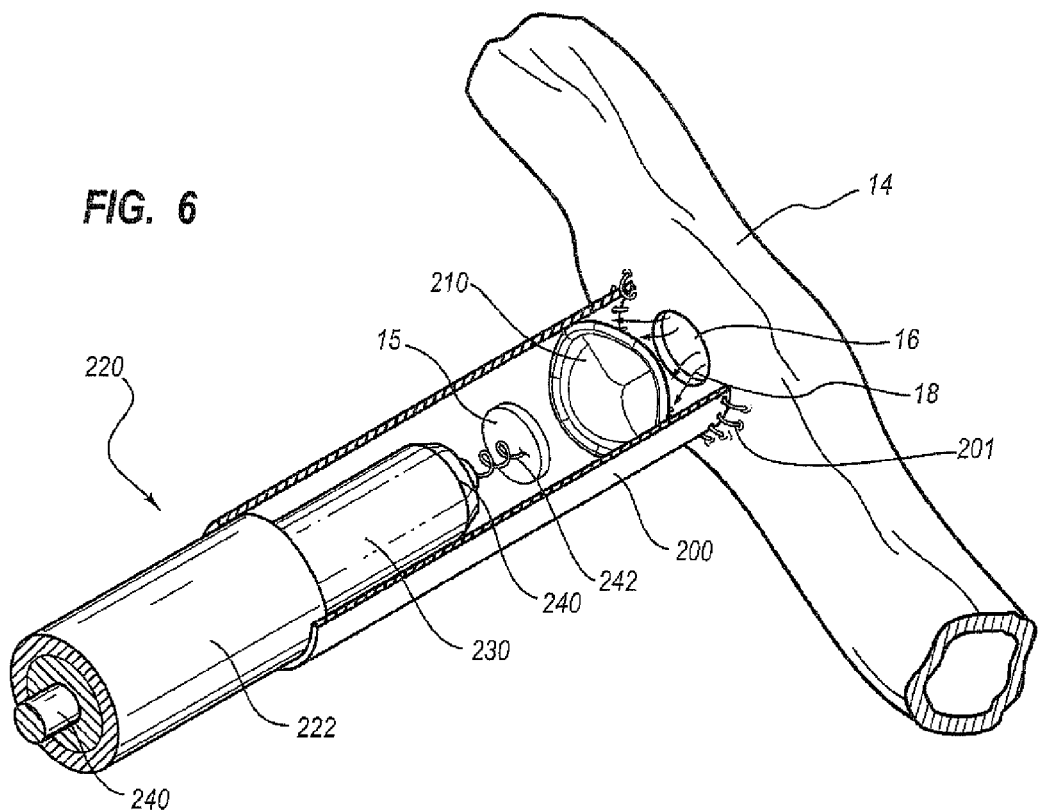
FIG. 6 is a perspective view of a valve sealing the tube illustrated in FIG. 5 against blood flowing out of an opening in an aorta.

FIG. 6 shows aorta 14 with an opening 16 that was cut open by cutting member 230. Corkscrew anchor 242 may be attached to a section of tissue is of aorta 14 that was cut out by cutting member 230. A physician may retract cardiovascular coring device 220 to pull tissue 15 away from aorta 14, as shown in FIG. 6. In some embodiments, tissue retraction member 240 may be retracted into cutting member 240 before cutting member 240 is retracted through valve 210. In various embodiments, tissue retraction member 240 may be completely retracted out of cutting member 230 and handle 240. Valve 210 may close after cutting member 240 is retracted through valve 210, thereby preventing blood 18 from flowing out of tube 200.

Figure 7:
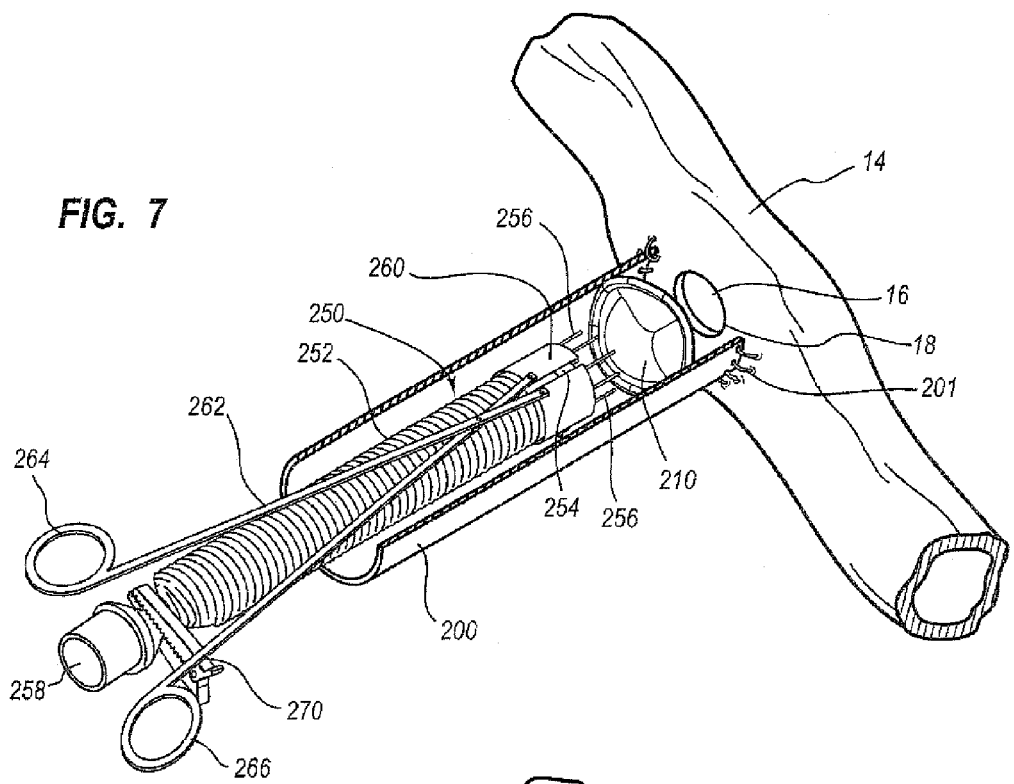
FIG. 7 is a perspective view of inserting a cardiovascular conduit section into the tube shown in FIG. 6.

FIG. 7 shows a cardiovascular conduit system 250 inserted into tube 200. Cardiovascular conduit system 250 may be inserted into tube 200 after cardiovascular coring device 220 is retracted from tube 200. Cardiovascular conduit section 250 may include a conduit 252, a connector 258, and a connector 254. Various examples of cardiovascular conduits and connectors are shown and discussed in U.S. patent application Ser. No. 12/340,280, filed on 19 Dec. 2008, and entitled "Systems, Apparatus, and Methods for Cardiovascular Conduits and Connectors," the disclosure of which is incorporated in its entirety in this reference.

Connector 254 may include expandable members 256. A retractable retaining member 260 may hold expandable members 256 in a delivery position while connector 254 is being implanted into aorta 14. Retractable retaining member 260 may be attached to handles 264 and 266 to allow a physician to control retractable retaining member 260.

A distal end of cardiovascular conduit section 250 may be sealed with a clamp 270. Clamp 270 may prevent blood from flowing out of cardiovascular conduit section 250 through connector 258 after cardiovascular conduit section 250 is attached to aorta 14. Clamp 270 may be any suitable size, shape, and/or configuration.

Figure 8:
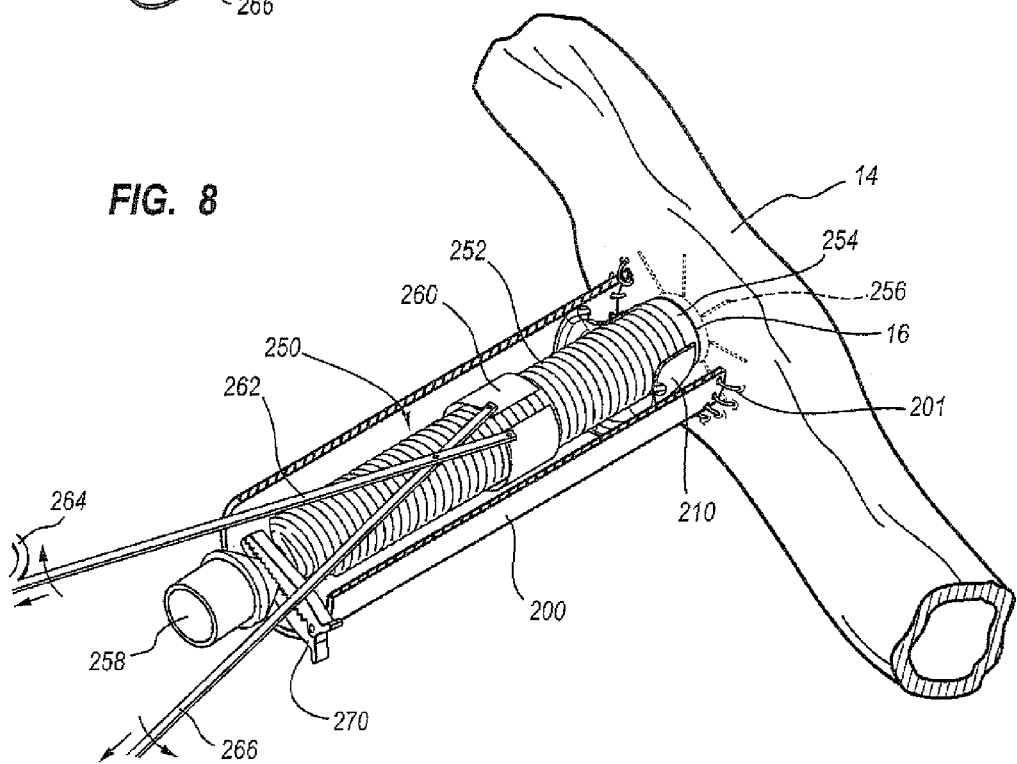
FIG. 8 is a perspective view of attaching a connector of the cardiovascular conduit system illustrated in FIG. 7 to an aorta.

As shown in FIG. 8, valve 210 may open to allow cardiovascular conduit section 250 pass through valve 210. As with cardiovascular coring device 220, cardiovascular conduit section 250 may be sealed to tube 200 by valve 210. Thus, valve 210 may prevent blood from leaking while cardiovascular conduit section 250 is being secured to aorta 14.

Connector 254 may pass through valve 210 and be partially inserted into opening 16 of aorta 14 such that expandable members 256 extend into aorta 14. A physician may then retract retaining member 260 to allow expandable members 256 to deploy and secure cardiovascular conduit system 250 to aorta 14, as shown in FIG. 8. After cardiovascular conduit section 250 is implanted in aorta 14, tube 200 may be removed from aorta 14. In embodiments where tube 200 was sutured to aorta 14, the sutures, such as sutures. 201, may be removed and tube 200 may be retracted from the implant site on aorta 14.

A physician may use a procedure similar to or the same as the procedure for implanting conduit section 250 in aorta 14 for implanting a cardiovascular conduit section in an apex of the heart at the left ventricle. For example, a tube may be attached to an apex of the heart. Then, a cutting member may be inserted through a valve in the tube to cut out a section of the apex of the heart. After the section of the heart and the cutting member are removed from the tube, a cardiovascular conduit section may be inserted through the tube and attached to the apex of the heart. This procedure (or similar procedures) for implanting cardiovascular conduit sections may be performed on the left ventricle of the heart, the right ventricle of the heart, the pulmonary artery, or any other blood vessel or cardiovascular organ.

Figure 9:
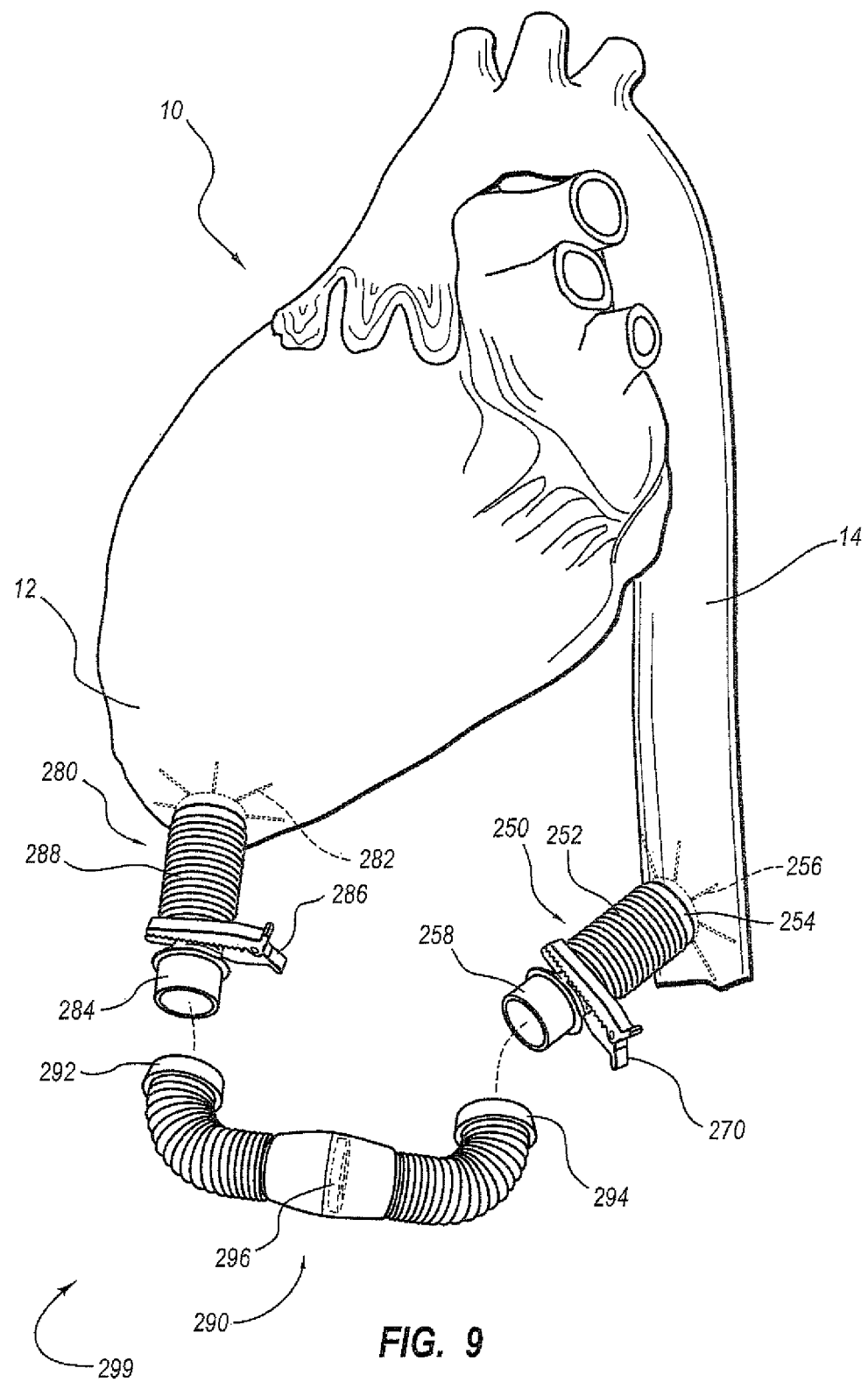
FIG. 9 is a perspective view of an exemplary cardiovascular conduit system according to certain embodiments.

FIG. 9 illustrates a cardiovascular conduit system 299. Cardiovascular conduit system 299 may include a cardiovascular conduit section 280 attached to a left ventricle 12 of heart 10 at an apex of heart 10. Cardiovascular conduit section 280 may include a connector 282, a connector 284, and a conduit 288. Connector 282 may be attached to left ventricle 12, and conduit 288 may be sealed against blood leakage between connectors 282 and 284 by clamp 286.

Cardiovascular conduit system 299 may also include cardiovascular conduit section 250, which includes connector 254, connector 258, and conduit 252. As previously noted, connector 254 may be attached to aorta 14. FIG. 9 also shows that cardiovascular conduit system 299 may include a cardiovascular conduit section 290. Cardiovascular conduit section 290 may include a connector 292, a connector 294, and a valve 296. Connector 292 may be dimensioned to attach to connector 284, and connector 294 may be dimensioned to attach to connector 258.

Figure 10:
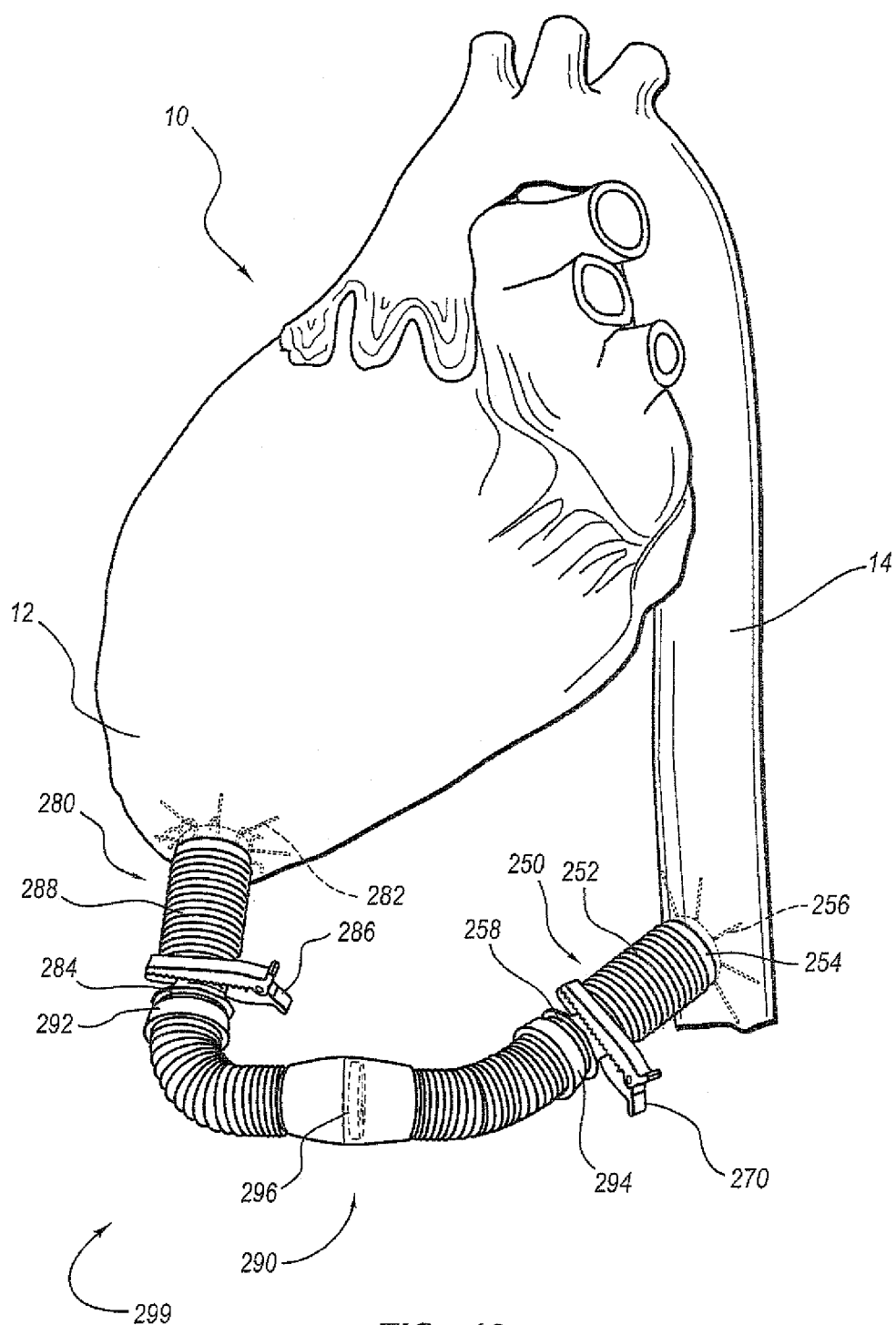
FIG. 10 is a perspective view of the cardiovascular conduit system illustrated in FIG. 9.
Figure 11:
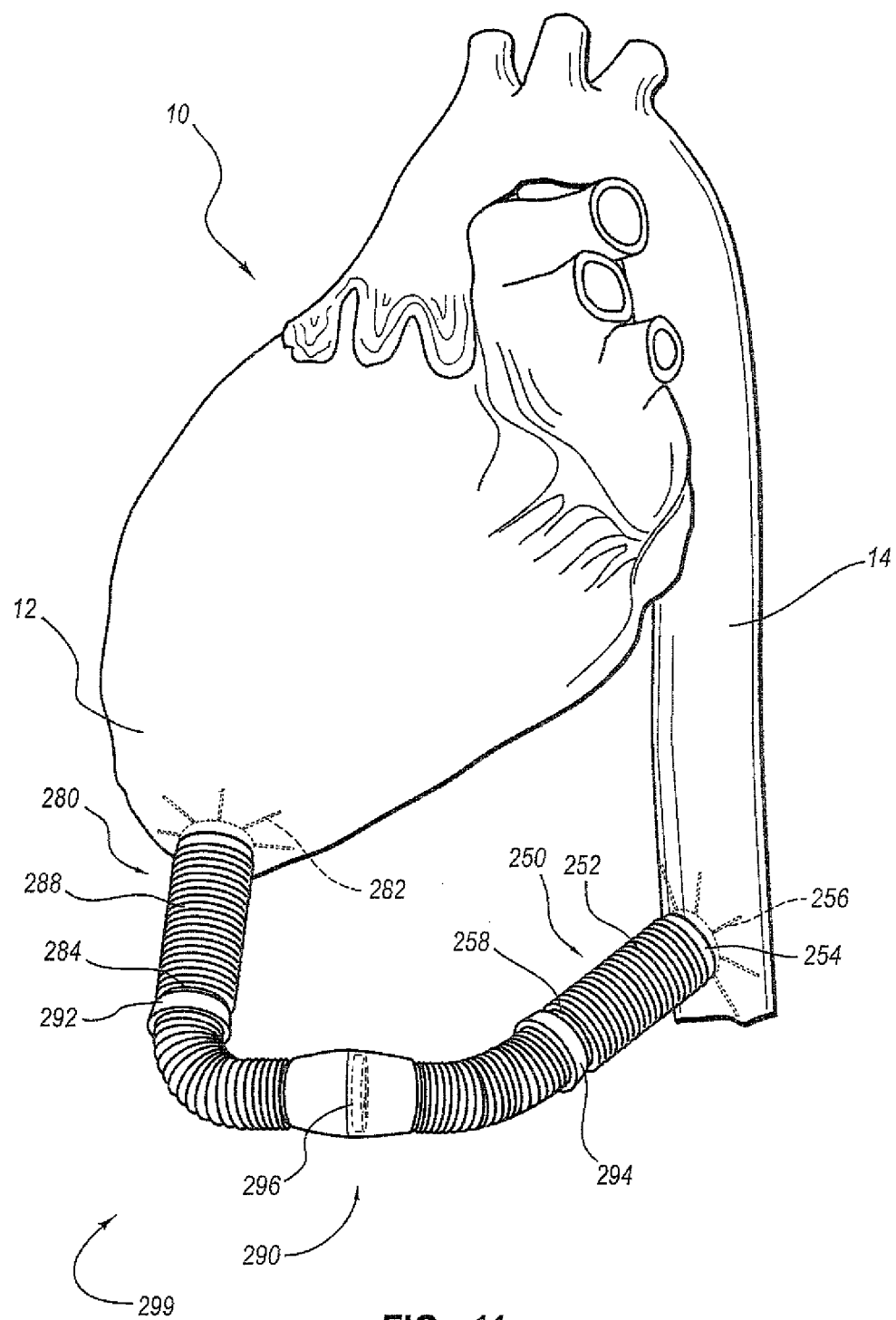
FIG. 11 is another perspective view of the cardiovascular conduit system illustrated in FIG. 9.

FIG. 10 shows cardiovascular conduit section 290 attached between cardiovascular conduit sections 250 and 280. Connector 292 may be attached to connector 284 to join cardiovascular conduit section 280 with cardiovascular conduit section 290. Similarly, connector 294 may be attached to connector 258 to join cardiovascular conduit sections 250 and 290. After cardiovascular conduit system 299 is assembled, clamps 270 and 286 may be removed to allow blood to begin to flow between left ventricle 12 and aorta 14. FIG. 11 shows cardiovascular conduit system 299 with clamps 270 and 286 removed. After clamps 270 and 286 are removed, blood may flow from left ventricle 12 to aorta 14 through valve 296.

Cardiovascular conduit systems, such as cardiovascular conduit system 299, may be attached between various cardiovascular organs. A cardiovascular organ may be any organ in a cardiovascular system. Cardiovascular organs include the heart and all the blood vessels (e.g., arteries and veins) in the cardiovascular system. Thus, the aorta and the pulmonary artery may be referred to as cardiovascular organs. According to some embodiments, blood vessels may also be referred to as vascular organs.

Figure 12:
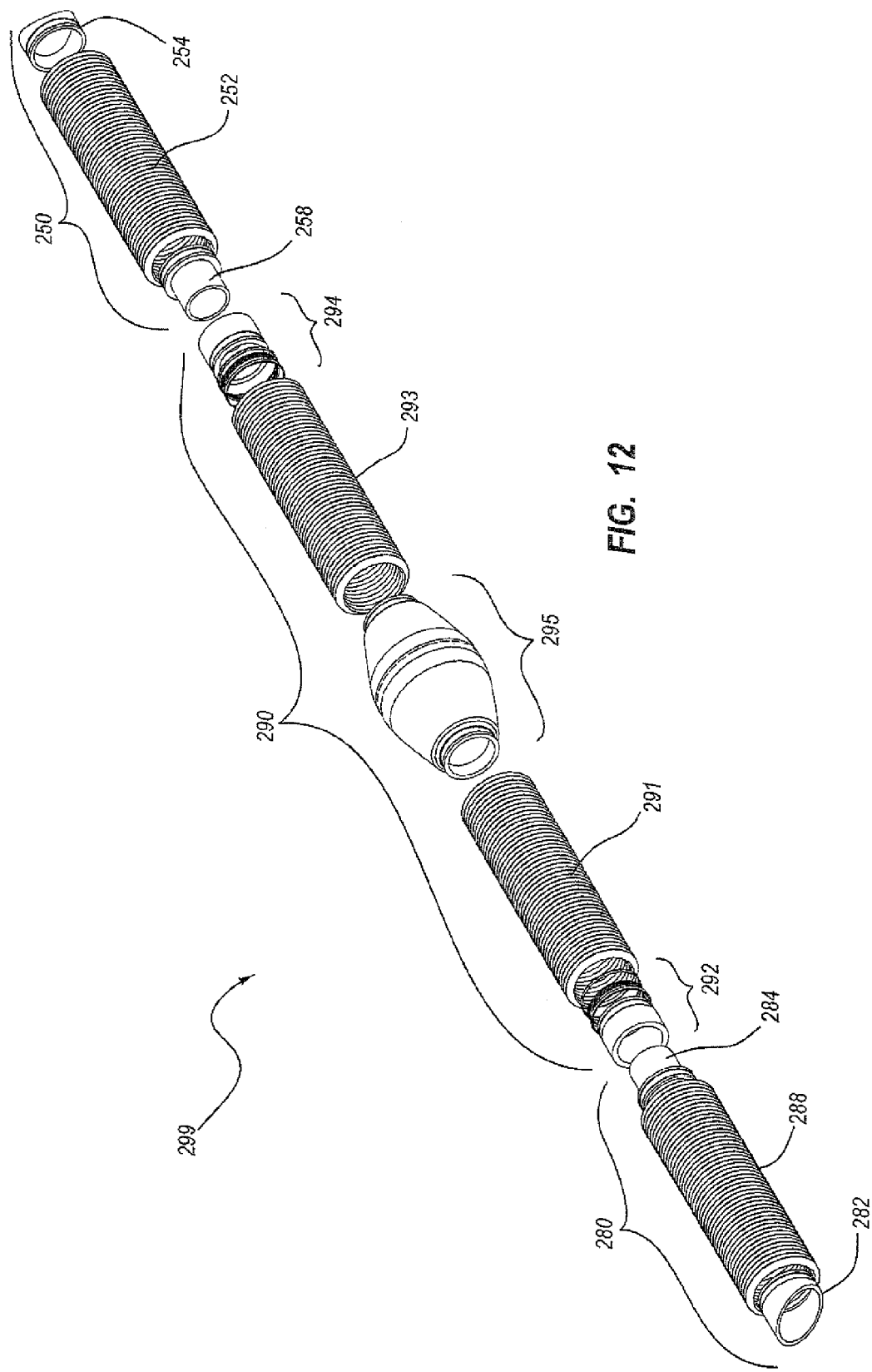
FIG. 12 is an exploded perspective view of a cardiovascular conduit system according to at least one embodiment.
Figure 13:
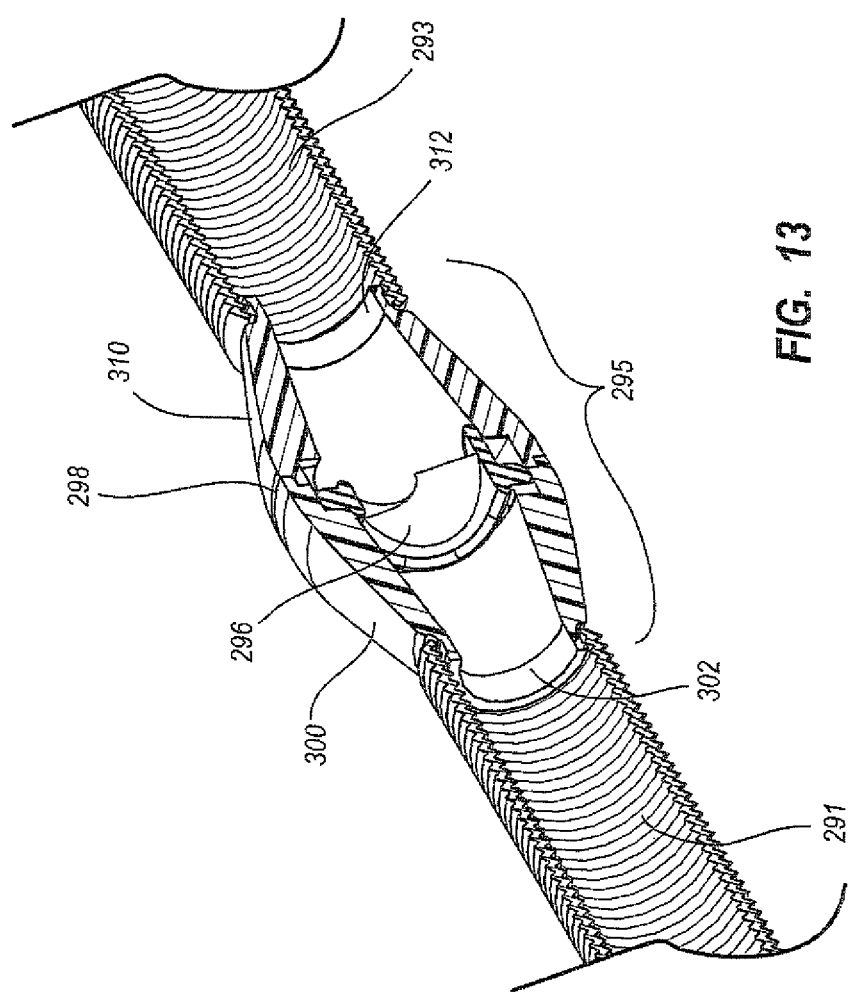
FIG. 13 is a cross-sectioned side view of a portion of the cardiovascular conduit system illustrated in FIG. 12.

FIG. 12 illustrates an exemplary cardiovascular conduit section 299 according to at least one embodiment. As illustrated in this figure, in at least one embodiment cardiovascular section 299 may comprise a cardiovascular conduit section 250, a cardiovascular conduit section 280, and a cardiovascular conduit section 290. Cardiovascular conduit section 290 may comprise a conduit 291, a conduit 293, and a cardiovascular valve assembly 295. As illustrated in FIG. 13, in at least one embodiment a first end 302 of cardiovascular valve assembly 295 may be removably attached to conduit 291. Similarly, a second end 312 of cardiovascular valve assembly 295 may be removably attached to conduit 293.

Cardiovascular valve assembly 295 generally represents any type or form of valve or valve assembly. In certain embodiments, cardiovascular valve assembly 295 may comprise a housing having a first portion 300 and a second portion 310. As will be discussed in greater detail below, first portion 300 may be removably attached to second portion 310. As illustrated in FIG. 13, in at least one embodiment cardiovascular valve assembly 295 may comprise a valve 296 and a cuff member 298.

Valve 296 generally represents any type or form of valve. Examples of valve 296 include, without limitation, a mechanical valve, a biological tissue valve, and a polymeric valve. In certain embodiments, valve 296 may be structured to allow fluid to flow through cardiovascular valve assembly 295 in a single direction. Valve 296 and cuff member 298 may be formed in any suitable shape and size and of any suitable material or combination of materials.

Figure 14:
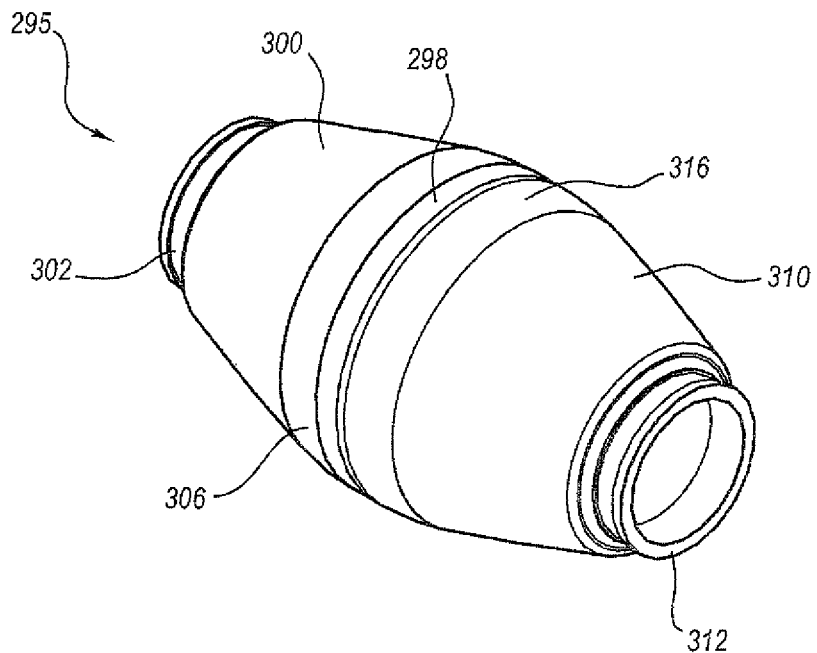
FIG. 14 is a perspective view of an exemplary cardiovascular valve assembly according to at least one embodiment.
Figure 15:
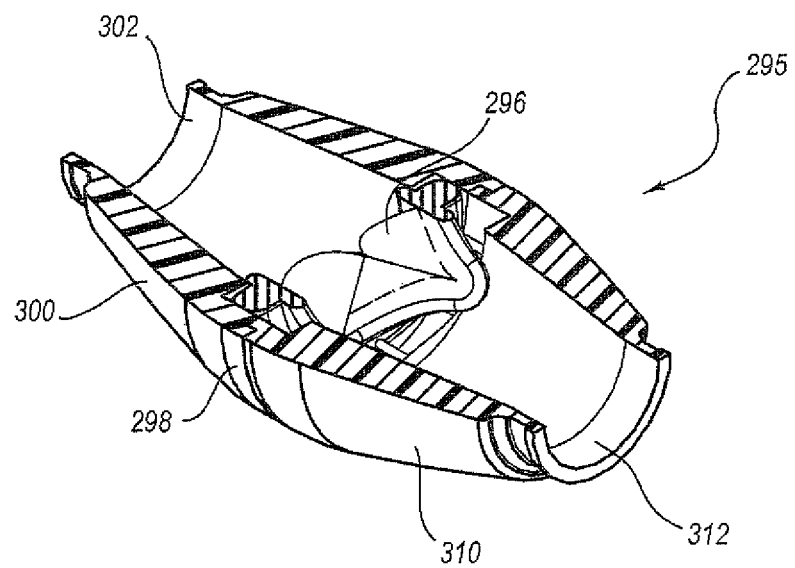
FIG. 15 is a cross-sectioned perspective view of the exemplary cardiovascular valve assembly illustrated in FIG. 14.

FIGS. 14 and 15 are illustrations of an exemplary cardiovascular valve assembly 295 according to at least one embodiment. As illustrated in these figures, in at least one embodiment cardiovascular valve assembly 295 may comprise a first portion 300 removably attached to a second portion 310. First portion 300 may comprise a first end 302 configured to be removably attached to a conduit, such as conduit 291 in FIG. 13, and a second end 306. Second portion 310 may comprise a first end 312 configured to be removably attached to a conduit, such as conduit 293 in FIG. 13, and a second end 316. In certain embodiments, second end 306 of first portion 300 may be configured to contact second end 316 of second portion 310.

Figure 16:
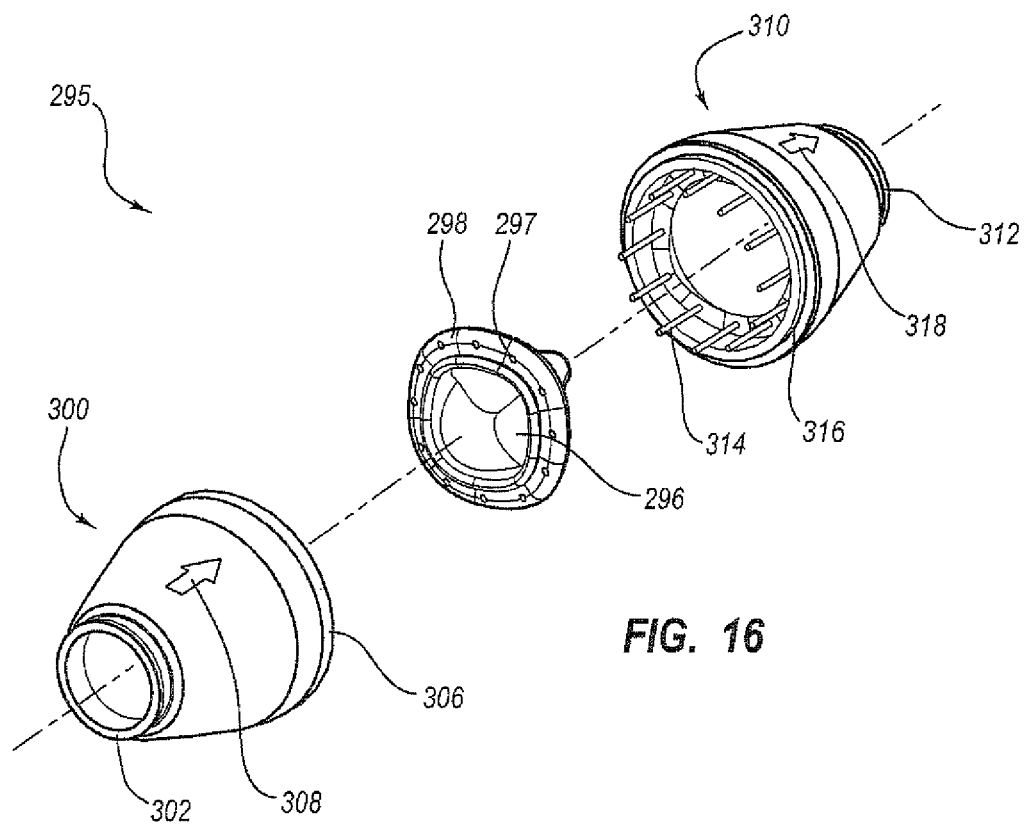
FIG. 16 is an exploded perspective view of an exemplary cardiovascular valve assembly according to at least one embodiment.
Figure 17:
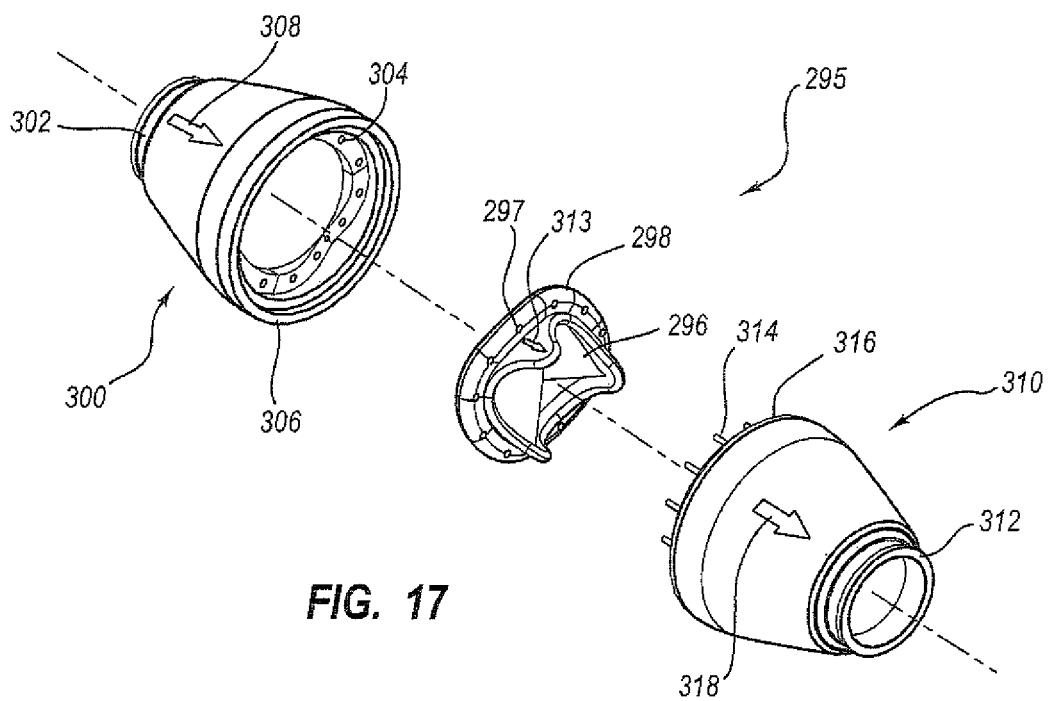
FIG. 17 is an additional exploded perspective view of the exemplary cardiovascular valve assembly illustrated in FIG. 16.
Figure 18:
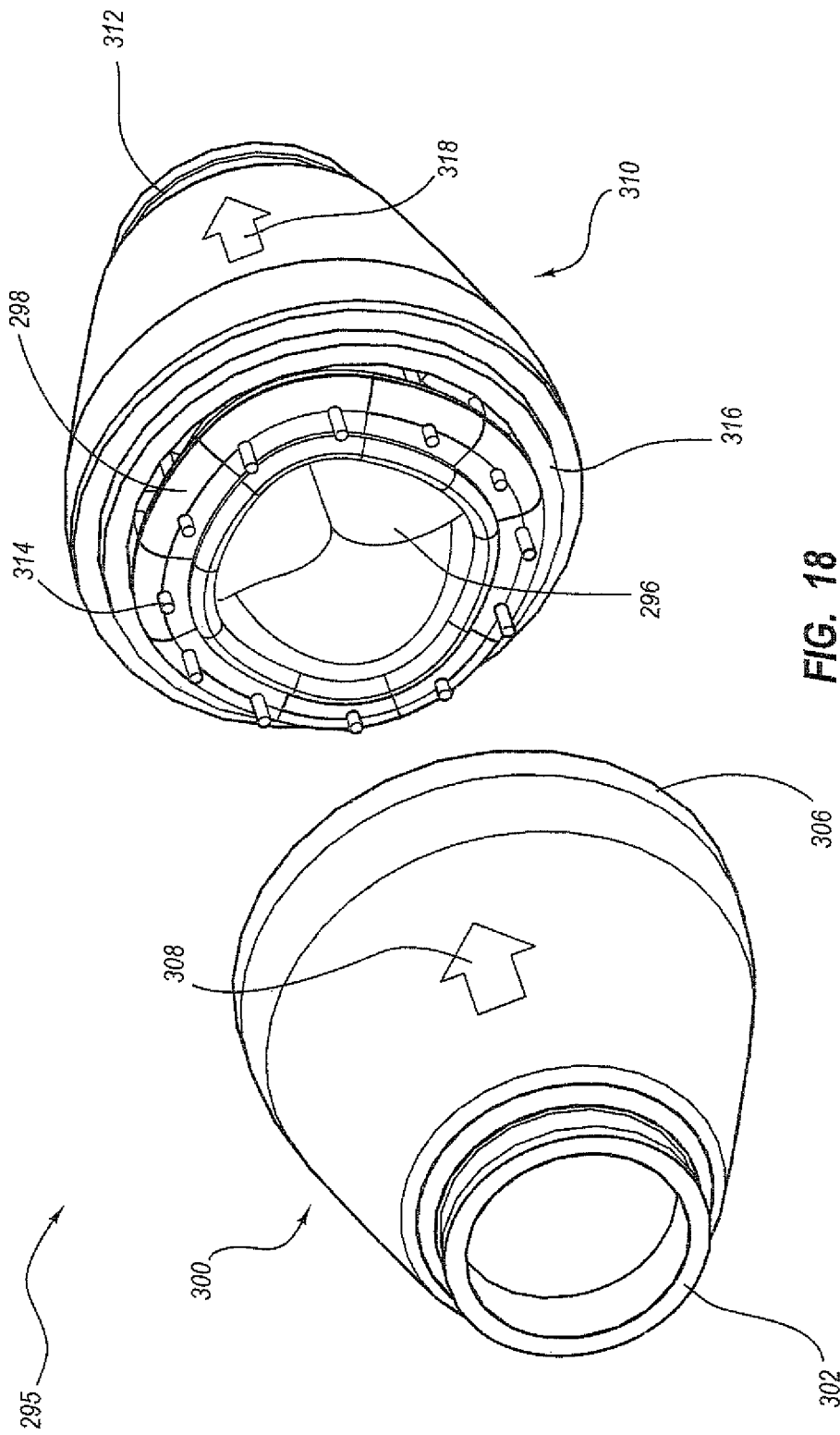
FIG. 18 is a partially assembled perspective view of the exemplary cardiovascular valve assembly illustrated in FIG. 16.

The first and second portions of a cardiovascular valve assembly may be removably attached in any number of ways and configurations. For example, as illustrated in FIGS. 16-18, first portion 300 may comprise a plurality of apertures 304 configured to receive a plurality of coupling structures 314 provided on second portion 310 to removably attach first portion 300 to second portion 310. Similarly, as illustrated in these figures, valve 296 may comprise a plurality of apertures 297 configured to receive the plurality of coupling structures 314 provided on second portion 310 to couple both valve 296 and first portion 300 to second portion 310. As clearly shown in FIGS. 12 and 16-18, the apertures 304, coupling structures 314, and valve 296 of the cardiovascular valve assembly 295 are positioned completely inside of the first and second portions 300, 310 when assembled (see FIG. 12).

In at least one embodiment, cardiovascular valve assembly 295 may comprise at least one identifying indicia configured to identify a desired direction for fluid flow. For example, as illustrated in FIGS. 16-18, first portion 300 may comprise a first identifying indicia 308. Similarly, second portion 310 may comprise a second identifying indicia 318 and valve 296 may comprise a third identifying indicia 313. In certain embodiments, identifying indicia 308, 318, and 313 may graphically illustrate the direction of fluid flow through cardiovascular valve assembly 295. Additionally or alternatively, valve 296 may be structured and/or sized to prevent valve 296 from being positioned within first portion 300 and/or second portion 310 in a manner that restricts fluid flow in a desired direction.

As detailed above, cuff member 298 may be formed in any shape or size and of any suitable material or combination of materials. In at least one embodiment, and as illustrated in FIGS. 12-18, cuff member 298 may be positioned between, and captured by, first portion 300 and second portion 310. In addition, in certain embodiments, cuff member 298 may comprise at least one seal member configured to prevent fluid flow from escaping cardiovascular valve assembly 295. Additionally or alternatively, one or more additional seal members may be positioned between first portion 300 and second portion 310 of cardiovascular valve assembly 295 to prevent fluid from escaping cardiovascular valve assembly 295.

Figure 19:
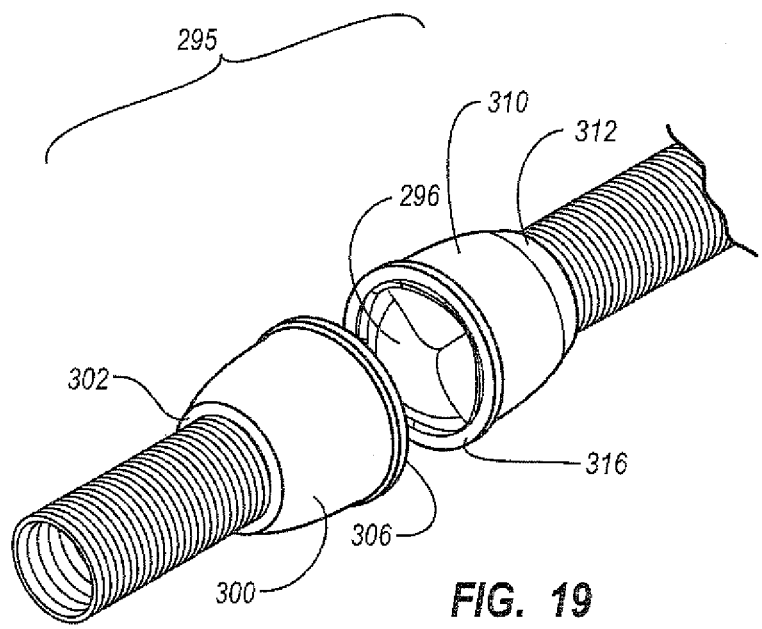
FIG. 19 is a cross-sectional side view of an exemplary cardiovascular valve assembly according to an additional embodiment.

Cardiovascular valve assembly 295 may be formed in any shape and size and of any suitable material or combination of materials. For example, as illustrated in FIG. 19, cardiovascular valve assembly 295 may comprise a substantially conical first portion 300 removably attached to a substantially conical second portion 310. In certain embodiments, first portion 300 may comprise a first end 302 and a substantially planar second end 306. Similarly, second portion 310 may comprise a first end 312 and a substantially planar second end 316. In at least one embodiment, substantially planar second end 306 of first portion 300 may be configured to contact substantially planar second end 316 of second portion 310.

Figure 20:
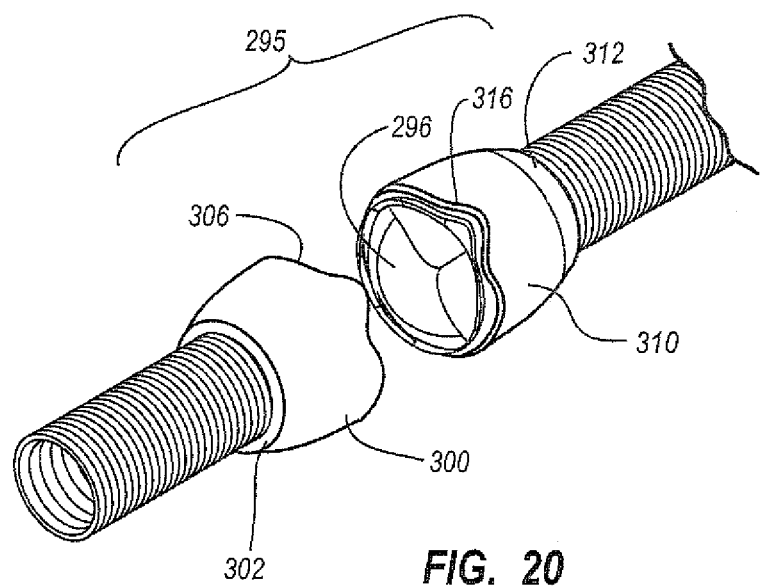
FIG. 20 is a side view of an exemplary cardiovascular valve assembly according to an additional embodiment.

In an additional embodiment, as illustrated in FIG. 20, cardiovascular valve assembly 295 may comprise a first portion 300 having a contoured end 306 configured to contact a contoured end 316 provided on second portion 310. In certain embodiments, contoured end 306 of first portion 300 may be formed in a complimentary manner so as to mate with contoured end 316 of second portion 310. Ends 306 and 316 of first and second portions 300 and 310, respectively, may be formed in any number of additional shapes and/or sizes. As clearly shown in FIGS. 16-17, there are three-dimensionally contoured surfaces in which the plurality of apertures 304 are formed on first portion 300 and from which the coupling structures 314 extend on second portion 310. These contoured surfaces are contoured in the longitudinal direction along the longitudinal axis of the valve assembly 295, have portions that fit between each other when assembled, and each comprise a plurality of depths relative to the longitudinal axis of the assembly.

Figure 21:
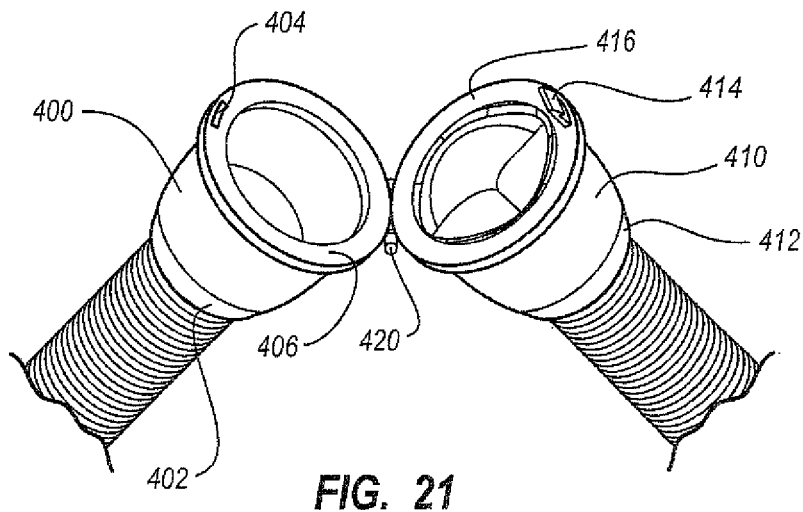
FIG. 21 is a perspective view of an exemplary cardiovascular valve assembly according to an additional embodiment.

FIG. 21 illustrates a cardiovascular valve assembly according to an additional embodiment. As illustrated in this figure, a cardiovascular valve assembly may comprise a first portion 400 removably attached to a second portion 410. In certain embodiments, first portion 400 may comprise a first end 402 and a second end 406. Similarly, second portion 410 may comprise a first end 412 and a second end 416. In at least one embodiment, a coupling structure 414 may be provided on second end 416 of second portion 410. In addition, an aperture 404 may be defined in the second end 406 of first portion 400. In at least one embodiment, aperture 404 may be structured to receive coupling structure 414 to couple first portion 400 to second portion 410. In addition, in certain embodiments, first portion 400 may be hingedly attached to second portion 410 by a hinge structure 420.

Figure 22:
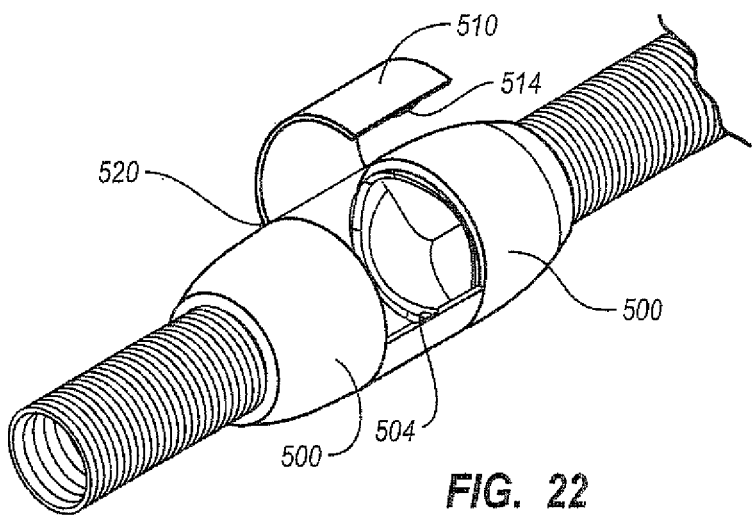
FIG. 22 is a perspective view of an exemplary cardiovascular valve assembly according to an additional embodiment.

FIG. 22 illustrates an exemplary cardiovascular valve assembly according to an additional embodiment. As illustrated in this figure, a cardiovascular valve assembly may comprise a first portion 500 and a second portion 510. In certain embodiments, second portion 510 may be hingedly attached to first portion 500 by hinge structure 520. In addition, as illustrated in this figure, second portion 510 may comprise a coupling structure 514. Similarly, first portion 500 may comprise a recess 504 configured to receive coupling structure 514 provided on second portion 510 to removably attach second portion 510 to first portion 500. As detailed above, first portion 500 and second portion 510 may be formed in any shape or size. For example, as illustrated in this figure, second portion 510 may be formed in the shape of a door configured to cover an opening defined in first portion 500.

Figure 23:
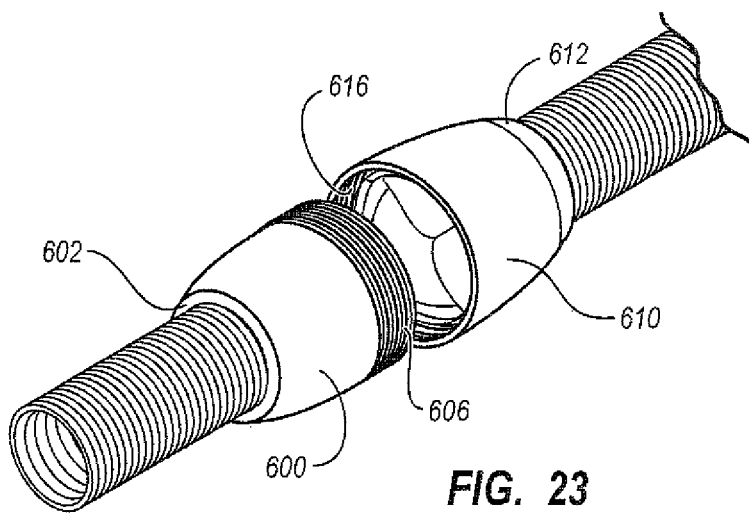
FIG. 23 is a perspective view of an exemplary cardiovascular valve assembly according to an additional embodiment.

FIG. 23 illustrates an exemplary cardiovascular valve assembly according to an additional embodiment. As illustrated in this figure, a cardiovascular valve assembly may comprise a first portion 600 having a first end 602 and a second threaded end 606. This exemplary cardiovascular valve assembly may also comprise a second portion 610 having a first end 612 and a second threaded end 616. In at least one embodiment, second threaded end 616 of second portion 610 may be configured to receive second threaded end 606 of first portion 600 to couple, first portion 600 to second portion 612.

Figure 24:
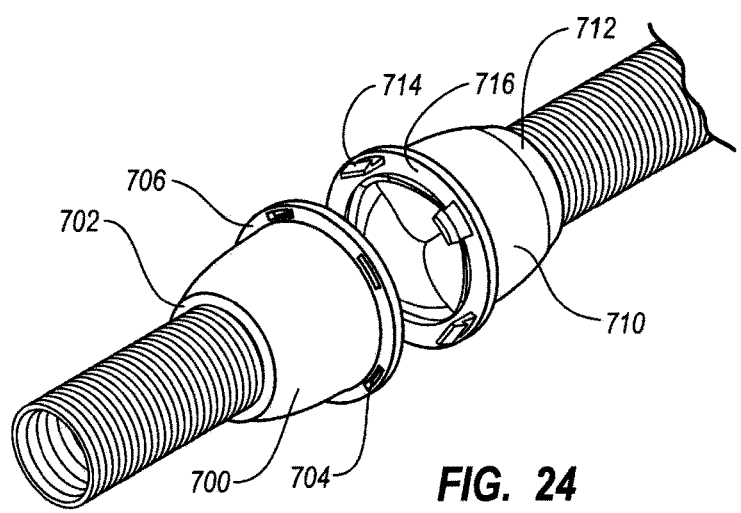
FIG. 24 is a perspective view of an exemplary cardiovascular valve assembly according to an additional embodiment.

FIG. 24 is an illustration of an exemplary cardiovascular valve assembly according to an additional embodiment. As illustrated in this figure, a cardiovascular valve assembly may comprise a first portion 700 having a first end 702 and a second end 706. This cardiovascular valve assembly may also comprise a second portion 710 having a first end 712 and a second end 716. In certain embodiments, a plurality of apertures 704 may be defined in second end 706 of first portion 700. Similarly, a plurality of complimentary-shaped coupling structures 714 may be provided on second end 716 of second end portion 710. In at least one embodiment, coupling structures 714 may be configured to snap-fit into recesses 704 defined in second end 706 of first portion 700 to couple second portion 710 to first portion 700. As with previous embodiments, coupling structure 714 and recesses 704 may be formed in any shape and/or size.

Figure 25:
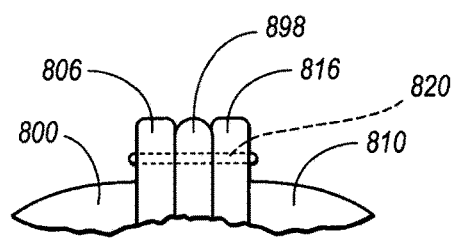
FIG. 25 is a top perspective view of a portion of an exemplary cardiovascular valve assembly according to an additional embodiment.
Figure 26:
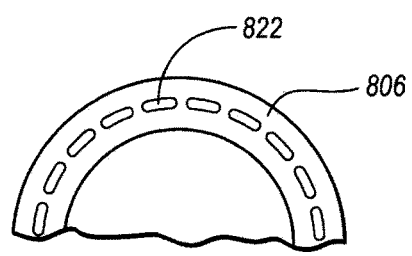
FIG. 26 is a front view of a portion of the exemplary cardiovascular valve assembly illustrated in FIG. 25.
Figure 27:
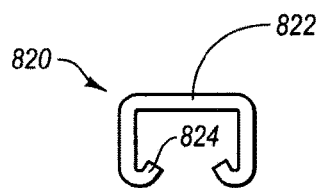
FIG. 27 is a perspective view of a portion of the exemplary cardiovascular valve assembly illustrated in FIG. 25.
Figure 28:
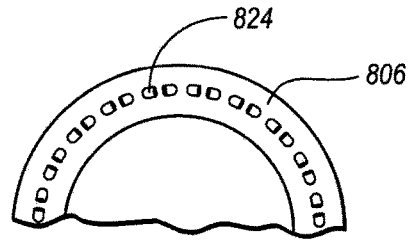
FIG. 28 is a back view of a portion of the exemplary cardiovascular valve assembly illustrated in FIG. 25.

FIGS. 25-28 illustrate a portion of an exemplary cardiovascular valve assembly according to an additional embodiment. As illustrated in FIG. 25, a first portion 800 may be attached to a second portion 810 of a cardiovascular valve assembly by inserting a staple or a retention device 820 through second end 806 of first portion 800, cuff member 898, and second end 816 of second portion 810. As best seen in FIG. 27, staple or retention member 820 may comprise a body 822 and one or more legs 824.

Figure 29:
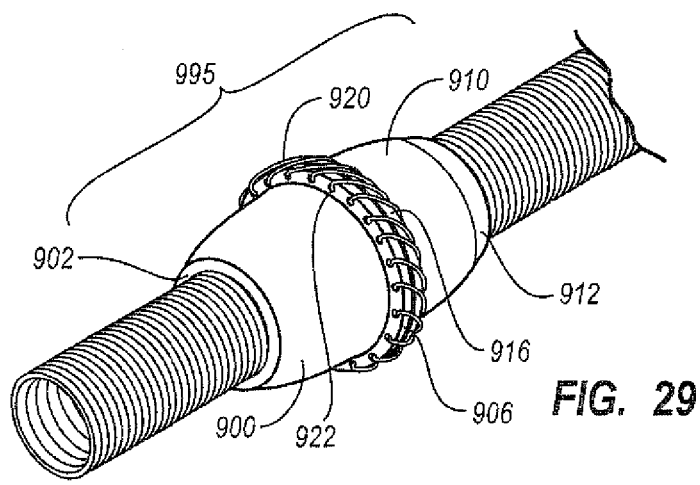
FIG. 29 is a perspective view of an exemplary cardiovascular valve assembly according to an additional embodiment.

FIG. 29 illustrates an exemplary cardiovascular valve assembly according to an additional embodiment. As illustrated in this figure, a cardiovascular valve assembly may comprise a first portion 900 having a first end 902 and a second end 906 and a second portion 910 having a first end 912 and a second end 916. In at least one embodiment, the second end 906 of first portion 900 may be brought into contact with second end 916 of second portion 910. In addition, in certain embodiments, a plurality of apertures 922 may be defined in second end 906 of first portion 900 and second end 916 of second portion 910. In certain embodiments, first portion 910 may be coupled to second portion 920 by inserting one more sutures 920 through apertures 922 defined in both second end 906 of first portion 900 and second end 916 of second portion 910.

Figure 30:
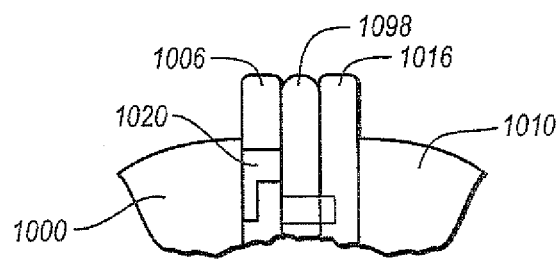
FIG. 30 is a perspective view of a portion of an exemplary cardiovascular valve assembly according to an additional embodiment.

In certain embodiments, a first portion of a cardiovascular valve assembly may be removably attached to a second portion of a cardiovascular valve assembly by rotating the first portion relative to the second portion. For example, as illustrated in FIG. 30, a first portion 1000 of a cardiovascular valve assembly may be removably attached to a second portion 1010 of a cardiovascular valve assembly by bringing ends 1006 and 1016 of first and second portions 1000 and 1010, respectively, into contact with a cuff member 1098, and then rotating first portion 1000 relative to second portion 1010 until a locking member 1020 locks into place. In this manner, first portion 1000 may be removably attached to second portion 1010.

Figure 31:
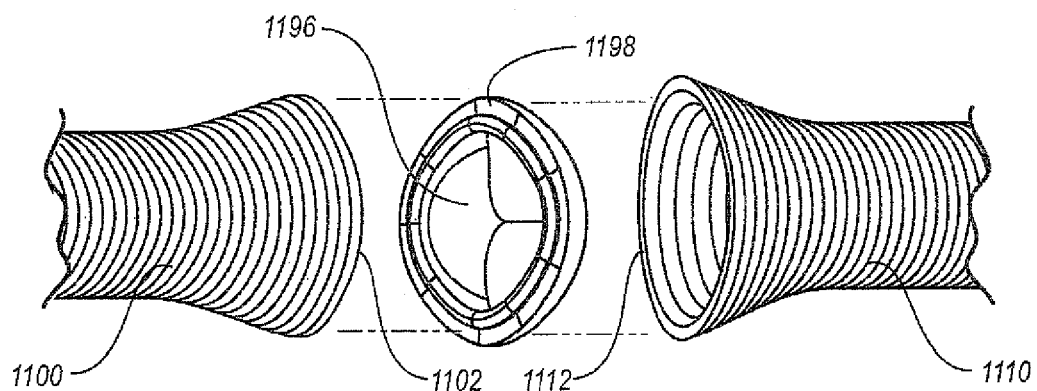
FIG. 31 is a perspective view of an exemplary cardiovascular valve assembly according to an additional embodiment.

FIG. 31 illustrates an exemplary cardiovascular valve assembly according to an additional embodiment. As illustrated in this figure, a cardiovascular valve assembly may comprise a first conduit 1100 having a first end 1102 and a second conduit 1110 having a first end 1112. In certain embodiments, ends 1102 and 1112 may be substantially conical in shape. In addition, a valve 1196 and a cuff member 1198 may be attached to ends 1102 and 1112. Valve 1196 and cuff member 1198 may be attached to ends 1102 and 1112 in any number of ways and configurations. For example, valve 1196 and cuff member 1198 may be sutured to ends 1102 and 1112.

Figure 32:
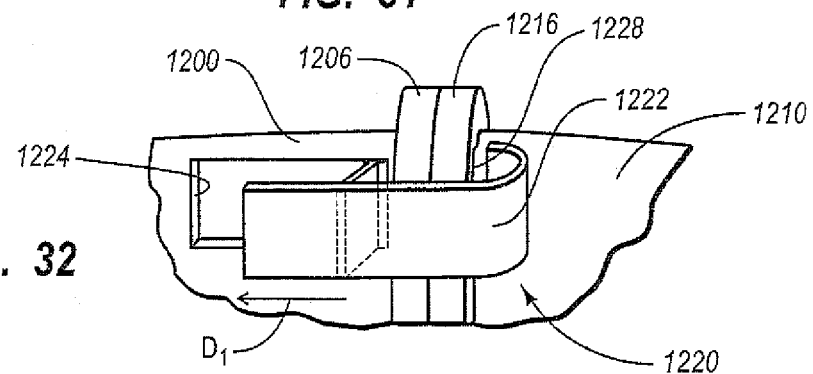
FIG. 32 is a perspective view of a portion of an exemplary cardiovascular valve assembly according to an additional embodiment.

FIG. 32 illustrates a portion of an exemplary cardiovascular valve assembly according to an additional embodiment. As illustrated in this figure, a cardiovascular valve assembly may comprise a first portion 1200 having an end 1206 and a second portion 1210 having an end 1216. In at least one embodiment, a locking tab assembly 1220 may be used to removably attach first portion 1200 to second portion 1210. As illustrated in this figure, a hook-shaped body 1222 of locking assembly 1220 may be configured to be inserted into an aperture 1228 defined in the end 1216 of second portion 1210 to removably attach first portion 1200 to second portion 1210. In certain embodiments, the exemplary configuration illustrated in FIG. 32 may prevent first portion 1200 from being accidentally detached from second portion 1210. In at least one embodiment, when locking assembly 1220 is not in use, body 1222 of locking assembly 1220 may be housed in a recess 1224 defined in first portion 1200.

Figure 33:
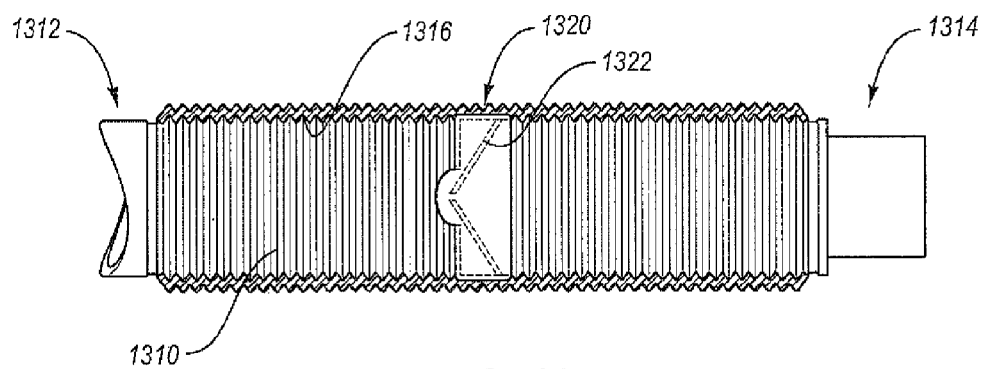
FIG. 33 is a cross-sectional side view of an exemplary cardiovascular valve assembly according to an additional embodiment.

FIG. 33 illustrates an exemplary cardiovascular valve assembly according to an additional embodiment. As illustrated in this figure, a cardiovascular valve assembly may comprise a conduit 1310 comprising a first connector 1312 and a second connector 1314. In at least one embodiment, a housing assembly 1320 may be positioned within conduit 1310. In addition, a mechanical valve 1322 may be positioned within housing assembly 1320. Housing assembly 1320 may be positioned within conduit 1310 in any number of ways and configurations. For example, in certain embodiments, housing assembly 1320 may be sutured to an internal surface 1316 of conduit 1310. In certain embodiments, the cardiovascular valve assembly illustrated in FIG. 33 may be pre-assembled for use by a physician during a medical procedure.

Figure 34:
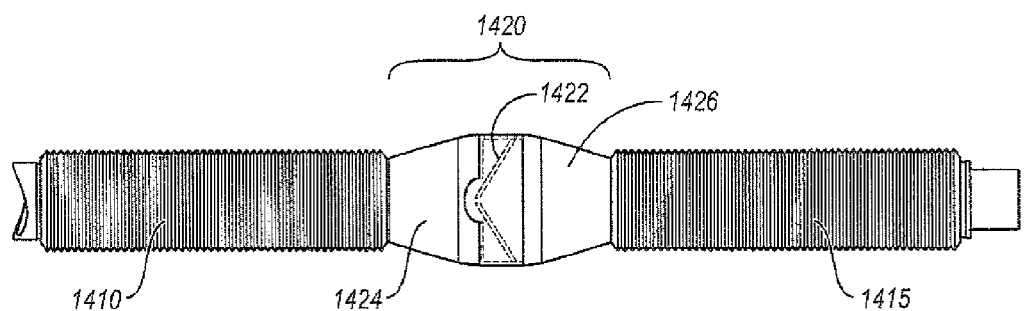
FIG. 34 is a side view of an exemplary cardiovascular valve assembly according to an additional embodiment.

As detailed above, a cardiovascular valve assembly may comprise any type or form of valve or valve assembly. For example, as illustrated in FIG. 34, a cardiovascular valve assembly may comprise a mechanical valve 1422. In certain embodiments, mechanical valve 1422 may be housed within a housing assembly 1420 comprising a first portion 1424 and a second portion 1426 removably attached to first portion 1424.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A cardiovascular valve assembly, comprising: a housing assembly, the housing assembly comprising:
    a first portion having first and second ends, a first outer surface, an internal cavity, and at least one coupling structure extending from a first undulating surface of the second end of the first portion, the at least one coupling structure and the first undulating surface being positioned inward from the first outer surface at the second end of the first portion;
    a second portion removably attached to the first portion and having first and second ends, a second outer surface, an internal cavity, and at least one coupling aperture positioned inward from the second outer surface within a second undulating surface at the second end of the second portion, the at least one coupling aperture being structured to receive the coupling structure to couple the first portion to the second portion, the at least one coupling structure being positioned completely within the first and second outer surfaces when the cardiovascular valve assembly is assembled;
    a valve positioned within the housing assembly and having at least one valve aperture defined therein and a cuff, the cuff being positioned between the first and second undulating surfaces when the cardiovascular valve assembly is assembled;

wherein the valve is structured to allow fluid to flow through the housing assembly in a single direction;

wherein the at least one coupling structure extends through the at least one valve aperture and through the at least one coupling aperture to couple the first portion and the valve to the second portion.

2. The cardiovascular valve assembly of claim 1, wherein the valve comprises at least one of:
   a mechanical valve;
   a biological tissue valve;
   a polymeric valve.

3. The cardiovascular valve assembly of claim 1, wherein:
   the first portion comprises a first connector, the first connector structured to removably attach the first portion to a first conduit;
   the second portion comprises a second connector, the second connector structured to removably attach the second portion to a second conduit.

4. The cardiovascular valve assembly of claim 1, wherein the valve is a biological tissue valve.

5. The cardiovascular valve assembly of claim 1, wherein the at least one valve aperture is defined in the cuff member.

6. The cardiovascular valve assembly of claim 5, wherein the at least one coupling structure extends axially from the first portion, and the at least one valve aperture and at least one coupling aperture are arranged axially.

7. The cardiovascular valve assembly of claim 1, further comprising at least one seal member positioned between the first portion and the second portion, the seal member configured to prevent fluid from escaping the housing assembly.

8. The cardiovascular valve assembly of claim 1, wherein, when the first portion is removably attached to the second portion, the first and second portions form a seal to prevent fluid from escaping the housing assembly.

9. The cardiovascular valve assembly of claim 1, further comprising at least one identifying indicia configured to identify a desired direction for fluid flow.

10. A cardiovascular valve assembly, comprising: a housing assembly, the housing assembly comprising:
    a first portion comprising first and second ends, a first outer surface, an internal cavity, and a plurality of coupling structures extending from a first three-dimensionally undulating surface, the first three-dimensionally undulating surface being contoured along a longitudinal axis extending through the housing assembly;
    a second portion comprising first and second ends, a second outer surface, an internal cavity, and a plurality of apertures positioned inward from the second outer surface in a second three-dimensionally undulating surface at the second end of the second portion and structured to receive the plurality of coupling structures to removably attach the first portion to the second portion, the second three-dimensionally undulating surface being contoured along the longitudinal axis extending through the housing assembly, the plurality of coupling structures being positioned completely within the first and second outer surfaces when the cardiovascular valve assembly is assembled;
    a valve positioned within the housing assembly;
    a cuff member around the valve, the cuff member being positioned between the first and second undulating surfaces when the cardiovascular valve assembly is assembled;
    at least one seal member positioned between the first portion and the second portion, the seal member configured to prevent fluid from escaping the housing assembly;
    at least one graphical illustration identifying indicia configured to indicate a desired direction for fluid flow;
    wherein the valve is structured to allow fluid to flow through the housing assembly in a single direction.

11. The cardiovascular valve assembly of claim 10, wherein the plurality of coupling structures extend axially from the first portion of the housing assembly.

12. The cardiovascular valve assembly of claim 10, wherein the plurality of apertures are arranged axially in the second portion of the housing assembly.

13. The cardiovascular valve assembly of claim 10, wherein the valve includes a valve opening that allows fluid to flow through the housing assembly, and a plurality of perimeter apertures, wherein the plurality of coupling structures extend through the plurality of perimeter apertures.

14. The cardiovascular valve assembly of claim 10, wherein the first and second three-dimensionally undulating surfaces are configured with a portion of one of the first and second three-dimensionally undulating surfaces positioned between portions of the other of the first and second three-dimensionally undulating surfaces when the valve assembly is assembled.

15. The cardiovascular valve assembly of claim 10, wherein the first and second three-dimensionally undulating surfaces each comprise a plurality of depths relative to the longitudinal axis of the housing assembly.

* * * * *